(12) United States Patent
Peterson et al.

(10) Patent No.: US 10,099,063 B2
(45) Date of Patent: Oct. 16, 2018

(54) MEDICAL MONITOR-DEFIBRILLATOR WITH DEFIBRILLATOR AND DATA OPERATIONS PROCESSORS

(71) Applicant: Physio-Control, Inc., Redmond, WA (US)

(72) Inventors: Ken Peterson, Bellevue, WA (US); Mitchell A Smith, Sammamish, WA (US); Denny Craig Edwards, Fall City, WA (US); Jeffery Scott Edwards, Bellingham, WA (US); Pablo Gonzalez-Gandolfi, Woodinville, WA (US); Rockland W Nordness, Redmond, WA (US); Matthew Lawrence Bielstein, Renton, WA (US); Clayton Ming Young, Redmond, WA (US); David B Stewart, Carnation, WA (US); Paul R Juhasz, Houston, TX (US); David Okey, Rockford, IL (US); Steven Witters, LaGrange, KY (US); Ira M Turner, Wallingford, CT (US)

(73) Assignee: PHYSIO-CONTROL, INC., Redmond, WA (US)

( * ) Notice: Subject to any disclaimer, the term of this patent is extended or adjusted under 35 U.S.C. 154(b) by 369 days.

(21) Appl. No.: 13/839,859

(22) Filed: Mar. 15, 2013

(65) Prior Publication Data
US 2014/0277227 A1 Sep. 18, 2014
US 2016/0121133 A9 May 5, 2016

Related U.S. Application Data

(60) Provisional application No. 61/667,320, filed on Jul. 2, 2012.

(51) Int. Cl.
*A61N 1/39* (2006.01)

(52) U.S. Cl.
CPC ......... *A61N 1/3993* (2013.01); *A61N 1/3987* (2013.01)

(58) Field of Classification Search
CPC .... G06F 1/1632; H05K 13/00; A61N 1/3937; A61N 1/3968; A61N 1/3975; H04B 7/26
(Continued)

(56) References Cited

U.S. PATENT DOCUMENTS 5,833,623 A * 11/1998 Mann et al. ................. 600/523
6,370,428 B1 * 4/2002 Snyder et al. .................. 607/5
(Continued)

FOREIGN PATENT DOCUMENTS

| EP | 0801959 A2 | 10/1997 |
|---|---|---|
| EP | 0923961 A1 | 6/1999 |
| WO | 13056194 A1 | 4/2013 |

OTHER PUBLICATIONS

Int'l Search Report and Written Opinion, PCT/US2012/071488, dated Feb. 8, 2013, 11 pages.
(Continued)

*Primary Examiner* — Carl H Layno
*Assistant Examiner* — Erin M Piateski
(74) *Attorney, Agent, or Firm* — Lane Powell PC

(57) ABSTRACT

A defibrillator is provided with two processors for enhancing the defibrillation process. A first processor is dedicated to controlling when an electrical charge is applied to a patient. A second processor is dedicated to data operations for enhancing the coaching of the defibrillation process. The second data processor is in communication with one or more external devices for transmission and receipt of network data for further enhancing the coaching process. The second data processor allows both the defibrillator to be maintained with updated network data and software and the one or more external devices to be maintained with updated defibrillator
(Continued)

data. Independent controllers provide multiple processing paths on critical charge and coaching functions; with the second data processor further providing redundancy control in the event of any malfunction of the first charge processor.

39 Claims, 11 Drawing Sheets

(58) Field of Classification Search
USPC .............................................................. 607/5
See application file for complete search history.

(56) References Cited

U.S. PATENT DOCUMENTS

| | | | |
|---|---|---|---|
| 7,006,865 B1* | 2/2006 | Cohen et al. ..................... 607/5 |
| 7,027,773 B1* | 4/2006 | McMillin ..................... 455/41.2 |
| 7,339,353 B1* | 3/2008 | Masias et al. ................. 320/138 |
| 7,528,572 B2* | 5/2009 | Masias et al. ................. 320/110 |
| 8,040,246 B2* | 10/2011 | Graves et al. ............. 340/573.1 |
| 8,054,177 B2* | 11/2011 | Graves et al. ........... 340/539.12 |
| 8,154,246 B1* | 4/2012 | Heitmann ..................... 320/109 |
| 2001/0031998 A1* | 10/2001 | Nelson et al. ................... 607/60 |
| 2001/0041920 A1* | 11/2001 | Starkweather et al. ........ 607/60 |
| 2002/0082480 A1* | 6/2002 | Riff et al. ..................... 600/300 |
| 2003/0028219 A1* | 2/2003 | Powers et al. .................... 607/5 |
| 2003/0097160 A1* | 5/2003 | Caby et al. ..................... 607/60 |
| 2003/0140274 A1* | 7/2003 | Neumiller et al. ............. 714/24 |
| 2003/0167074 A1* | 9/2003 | Merry ............................... 607/5 |
| 2003/0212311 A1* | 11/2003 | Nova et al. ................... 600/300 |
| 2004/0133244 A1* | 7/2004 | Vaisnys et al. ................... 607/5 |
| 2005/0021370 A1* | 1/2005 | Riff et al. ......................... 705/2 |
| 2005/0193081 A1* | 9/2005 | Gruber et al. ................. 709/212 |
| 2005/0226201 A1* | 10/2005 | McMillin ..................... 370/348 |
| 2006/0149321 A1* | 7/2006 | Merry et al. ....................... 607/5 |
| 2006/0149323 A1* | 7/2006 | Merry et al. ....................... 607/5 |
| 2006/0161214 A1* | 7/2006 | Patel .............................. 607/32 |
| 2006/0173498 A1* | 8/2006 | Banville et al. .................. 607/5 |
| 2006/0287694 A1* | 12/2006 | Almendinger et al. ........ 607/60 |
| 2007/0032830 A1* | 2/2007 | Bowers ............................. 607/5 |
| 2008/0015645 A1* | 1/2008 | Kelly et al. ....................... 607/5 |
| 2008/0174278 A1* | 7/2008 | Masias et al. ................. 320/138 |
| 2009/0264948 A1* | 10/2009 | Tamura et al. ................... 607/5 |
| 2009/0295326 A1* | 12/2009 | Daynes et al. ................ 320/106 |
| 2010/0114326 A1* | 5/2010 | Winslow et al. ........... 623/23.42 |
| 2010/0241181 A1* | 9/2010 | Savage et al. .................... 607/5 |
| 2011/0015701 A1* | 1/2011 | KenKnight et al. ............ 607/60 |
| 2011/0167250 A1* | 7/2011 | Dicks et al. ...................... 713/2 |
| 2011/0179405 A1* | 7/2011 | Dicks et al. ................... 717/168 |
| 2011/0208259 A1* | 8/2011 | Pearce et al. ..................... 607/5 |
| 2011/0230734 A1* | 9/2011 | Fain et al. ..................... 600/302 |
| 2011/0273287 A1* | 11/2011 | LaLonde et al. ........ 340/539.12 |
| 2011/0295078 A1* | 12/2011 | Reid et al. .................... 600/300 |
| 2011/0313494 A1* | 12/2011 | Freeberg ........................ 607/60 |
| 2012/0022606 A1* | 1/2012 | Walker et al. .................... 607/3 |
| 2013/0096649 A1 | 4/2013 | Martin et al. |

OTHER PUBLICATIONS

Int'l Search Report and Written Opinion, PCT/US2012/071436, dated Apr. 10, 2013, 13 pages.
Int'l Search Report and Written Opinion, PCT/US2012/071461, dated Apr. 10, 2013, 14 pages.
ISR and Written Opinion, PCT/US12/71450, dated May 24, 2013 (10 pages).

* cited by examiner

DEFIBRILLATION SCENE

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

TWO MAIN TYPES OF
EXTERNAL DEFIBRILLATORS

COMPONENTS OF EXTERNAL DEFIBRILLATOR

MEDICAL MONITOR-DEFIBRILLATOR WITH DEFIBRILLATOR AND DATA OPERATIONS PROCESSORS

CROSS REFERENCE TO RELATED PATENT APPLICATIONS

This patent application may be found to be related to U.S. patent application Ser. No. 13/836,304, entitled "Clinical Dashboard for Medical Device", filed contemporaneously herewith in the name of Randy L. Merry et al.; and U.S. patent application Ser. No. 13/836,769, entitled "Decision Support Tool For Use With a Medical Monitor-Defibrillator", filed contemporaneously herewith in the name of Ken Peterson et al.

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body and from where it returns to the right atrium to start the oxygenation-deoxygenation cycle of the blood all over again.

The heart chambers pump because of the heart's electrical control system. More particularly, the sinoatrial (SA) node generates an electrical impulse, which generates further electrical signals. These further signals cause the above-described contractions of the various chambers in the heart to occur in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In an SCA, the heart fails to pump blood effectively, and, if not corrected, can result in death. It is estimated that SCA results in more than 250,000 deaths per year in the United States alone. Further, an SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not corrected in time, will result in death, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume normal contractions in pumping blood. If VF is not terminated, the shock may be repeated, often at escalating energies.

A challenge with defibrillation is that the electrical shock must be administered very soon after the onset of VF. There is not much time to do this since the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because the blood flow has stopped. They should receive therapy quickly after the onset of VF or they will die.

For a VF victim without an ICD, a different type of defibrillator can be used, which is called an external defibrillator. External defibrillators have been made portable, so they can be brought to a potential VF victim quickly enough to revive them.

During VF, the person's condition deteriorates because the blood is not flowing to the brain, heart, lungs, and other organs. The blood flow must be restored, if resuscitation attempts are to be successful.

Cardiopulmonary Resuscitation (CPR) is one method of forcing blood to again flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows down the deterioration that would otherwise occur while a defibrillator is being retrieved. For patients with an extended down-time, survival rates are higher if CPR is administered prior to defibrillation.

Advanced medical devices may be used to assist the CPR process by coaching a rescuer who performs CPR. For example, a medical device can issue instructions, and even prompts, for the rescuer to perform CPR more effectively.

While some advanced medical devices provide coaching, defibrillator operators may benefit from improved coaching and defibrillation charge management.

BRIEF SUMMARY

The present description gives instances of devices, systems, software and methods, the use of which may help overcome problems and limitations of the prior art.

More specifically, a defibrillator is provided with two processors for enhancing the defibrillation process. A first processor is dedicated to controlling when an electrical charge is applied to a patient. A second processor is dedicated to data operations for enhancing the monitoring and diagnostic capability, interventional treatment capability, and the coaching capability of the defibrillation process. The second processor is in communication with one or more external devices for transmission and receipt of network data for further enhancing the coaching process. The second processor allows the defibrillator to be maintained with updated network data and software and the one or more external devices with updated defibrillator data. Independent controllers provide multiple processing paths for monitoring and diagnostic capability, interventional treatment capability, and coaching capability, leaving the defibrillator processor to focus on critical charge and defibrillation functions.

These and other features and advantages of this description will become more readily apparent from the following Detailed Description, which proceeds with reference to the drawings, in which:

BRIEF DESCRIPTION OF THE DRAWINGS

FIG. 1 is an illustrative diagram of a scene showing the use of an external defibrillator to save the life of a person according to this disclosure.

FIG. 2 is a table listing two illustrative types of the external defibrillator shown in FIG. 1, and who they might be used by.

DETAILED DESCRIPTION

Figures 1, 2:
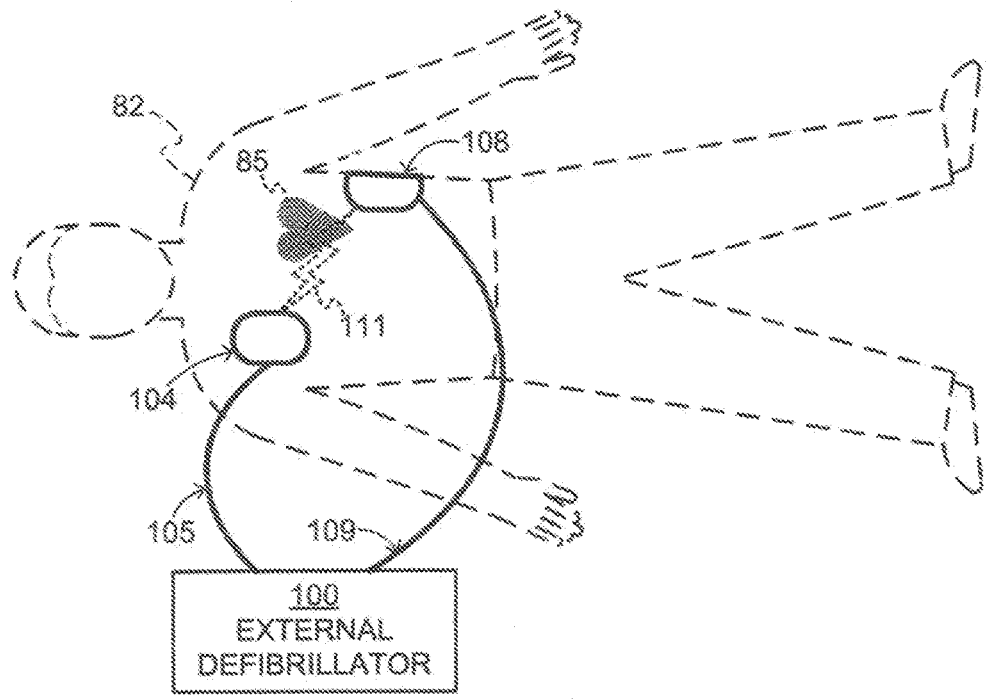

FIG. 1 is a diagram of a defibrillation scene showing the use of an external defibrillator to save the life of a person according to this disclosure. As shown, a person 82 is lying on his back. Person 82 could be a patient in a hospital, or someone found unconscious, and then turned over onto his back. Person 82 is experiencing a condition in their heart 85, which could be Ventricular Fibrillation (VF).

A portable external defibrillator 100 has been brought close to person 82. At least two defibrillation electrodes 104, 108 are typically provided with external defibrillator 100, and are sometimes called electrodes 104, 108. Electrodes 104, 108 are coupled together with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, also goes through heart 85, in an attempt to restart it, for saving the life of person 82.

Defibrillator 100 can be one of different types, each with different sets of features and capabilities. The set of capabilities of defibrillator 100 is determined based upon who would use it and what training they would be likely to have. Examples are now described.

FIG. 2 is a table listing two typical types of external defibrillators, and who they are primarily intended to be used by. A first type of defibrillator 100 is generally called a defibrillator-monitor, because the defibrillator part is typically formed as a single unit with a patient monitor part. A defibrillator-monitor is sometimes called monitor-defibrillator. A defibrillator-monitor is intended to be used by persons in the medical profession, such as doctors, nurses, paramedics, emergency medical technicians, etc. who may be trained to provide medical treatment to the patient during a defibrillation process based upon information provided by the monitor. Such a defibrillator-monitor is intended to be used in a pre-hospital or hospital scenario.

The defibrillator part may be dedicated to a particular mode of operation. Alternatively, the defibrillator part may be configured to operate in more than one modes of operation. One mode of operation of the defibrillator part may be that of an automated defibrillator, which can determine whether a shock is needed and, if so, charge to a predetermined energy level and instruct the user to administer the shock. Another mode of operation may be that of a manual defibrillator, where the user determines the need and controls administering the shock. In this embodiment, one illustrative defibrillator is configured to enable both automated defibrillation and manual defibrillation modes of operation depending upon the selection of the user. As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not trained in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Often, the people who will first reach the VF sufferer may not be in the medical profession.

Increasing awareness of the short survival time of a patient experiencing a VF, has resulted in AEDs being deployed more pervasively in public or semi-public spaces, enabling members of the public to use one provided they have obtained first aid and CPR/AED training. In this way, defibrillation can be administered sooner after the onset of VF, to hopefully be effective in rescuing the person.

There are additional types of external defibrillators, which are not listed in FIG. 2. For example, a hybrid defibrillator can have aspects of an AED, and also of a defibrillator-monitor. An illustrative example may be an AED provided with an ECG monitoring capability.

Figure 3:
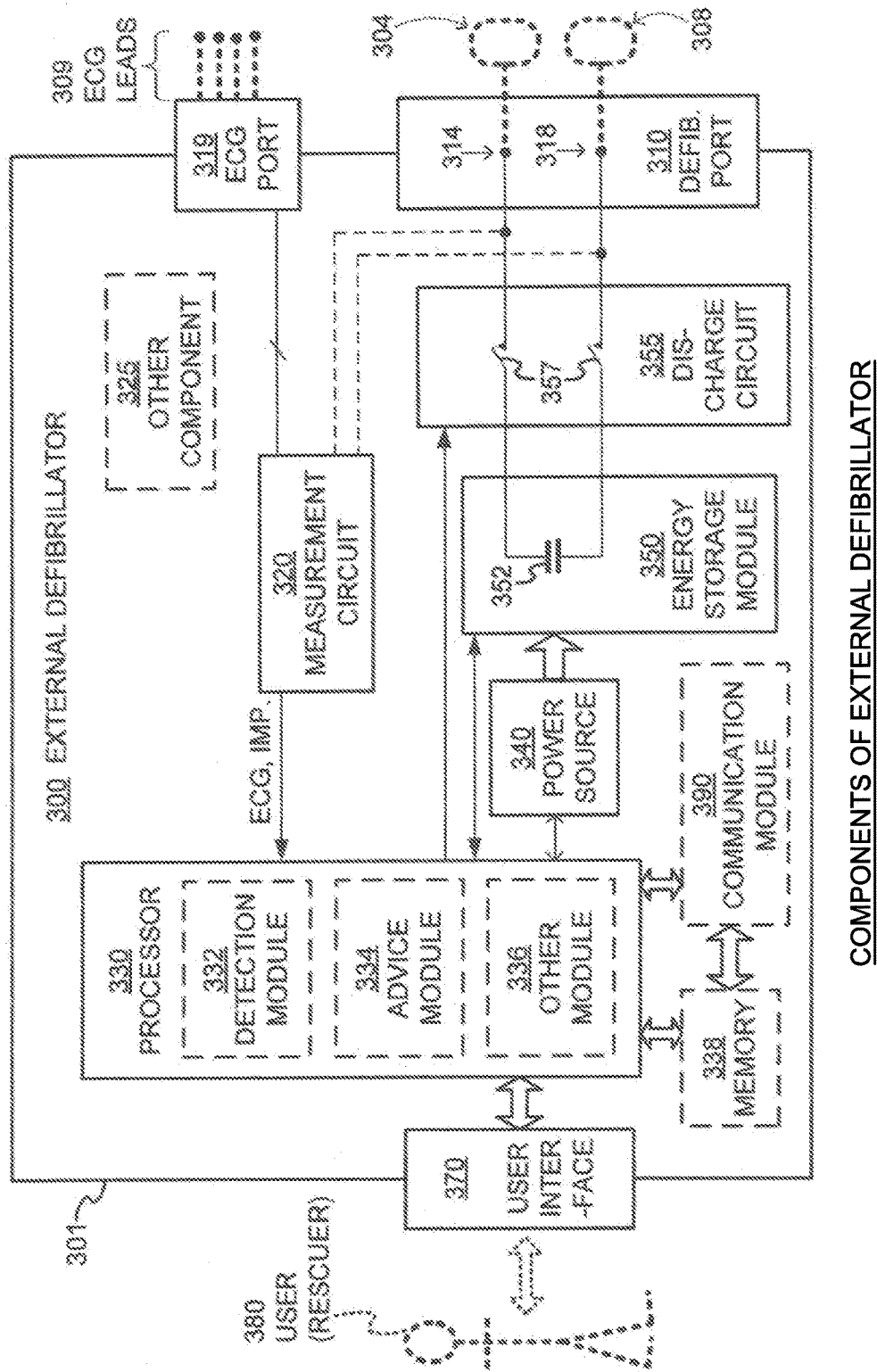
FIG. 3 is a diagram showing components of an external defibrillator, such as the one shown in FIG. 1, configured in an illustrative embodiment according to this disclosure.

FIG. 3 is a diagram showing components of an external defibrillator 300 configured in an illustrative embodiment according to this disclosure. These components can be configured, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, which may be configured as a socket (not shown) in housing 301. Defibrillation port 310 includes nodes 314, 318. Defibrillation electrodes 304, 308, which can be similar to electrodes 104, 108 in FIG. 1, can be plugged into defibrillation port 310, so as to make electrical contact with nodes 314, 318, respectively. It is also possible that electrodes can be hard-wired to defibrillation port 310, etc. Either way, defibrillation port 310 can be used for guiding to person 82 via electrodes an electrical charge that has been stored in defibrillator 300, as discussed below.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or a signal taken from a different number of leads. Moreover, a defibrillator-monitor could have additional ports (not shown), and another component 325 for the above described additional features, such as for receipt of patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals in this case through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 may include a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at a piece of instructional advice based on outputs of detection module 332. Advice module 334 can include a Shock Advisory Algorithm residing in a memory unit (not shown) in the advice module for instructing the processor to implement decision rules, etc. Alternatively, the Shock Advisory Algorithm may reside in part or in whole on a memory 338 of the defibrillator. The instruction to the processor can be to shock, to not shock, to administer other forms of therapy, and so on. If the instruction to the processor is to shock, in some external defibrillator embodiments, the processor is configured to report that instruction to the user via user interface 370, and to prompt the user to do it. In other embodiments, the processor may be configured to execute the instructional advice, by administering the shock. If the instructional advice is to administer CPR, the processor may be configured to enable defibrillator 300 to issue prompts to administer CPR, etc.

Processor 330 can include additional modules, such as module 336, for other functions. In addition, if other component 325 is provided, it may be operated in part by processor 330 or by another processor.

Defibrillator 300 optionally further includes the memory 338, which can work together with processor 330. Memory 338 may be implemented in any number of ways. Such ways include, by way of example and not of limitation, nonvolatile memories (NVM), read-only memories (ROM), random access memories (RAM), any combination of these, etc. Memory 338, if provided, may include programs containing instructions for execution by processor 330 or other processors that may be included in the external defibrillator. The programs provide instructions for execution by the processor 330, and can also include instructions regarding protocols and decision making analytics, etc. that can be used by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include an AC power override, whereby AC power, instead of power from power source 340 is delivered to an energy storage module 350 when AC power is available. In some embodiments, power source 340 is controlled by processor 330.

Defibrillator 300 additionally includes the energy storage module 350. Module 350 is where electrical energy is stored in preparation for a sudden discharge to administer a shock. The charge to module 350 from power source 340 to the right amount of energy can be controlled by processor 330. In typical implementations, module 350 includes one or more capacitors 352, and may include other circuitry.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and in other ways well known in the art.

Defibrillator 300 further includes the user interface 370 for user 380. User interface 370 can be made in any number of ways. For example, interface 370 may include a screen, to display a parameter of a patient that is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other devices. Such communication can be performed wirelessly, or via wire, or by infrared communication, and so on. In this way, data can be communicated from the defibrillator 300 to external devices, such as patient data, incident information, therapy attempted, CPR performance, and so on.

Having thus introduced background on the general operation of a defibrillator, we now turn to features that are provided by this disclosure. Generally, FIGS. 4-13 teach a system and method for splitting the processing occurring within a defibrillator between two processors. More specifically, the defibrillator operations are split between a first processor dedicated to controlling when an electrical charge is applied to a patient and a second processor dedicated to data operations for enhancing the monitoring and diagnostic capability, interventional treatment capability, and the coaching capability of the defibrillation process. By splitting the defibrillator processing between two processors the first processor may be dedicated to controlling when an electrical charge is applied to a patient and the second processor may handle the majority of advanced features. The second data processor is in communication with one or more external devices for transmission and receipt of network data for further enhancing the coaching process.

The external device may be a printer, a tablet, a mobile device, a smart phone, an external computer, a smart cart, etc. A smart cart is a device configured to include basic inventory management resources that are available in the event of a crash or other accident. In addition, the data received by the data processor from one or more external devices may provide use in enhancing the monitoring and diagnostic capability, interventional treatment capability, and the coaching capability of the defibrillator. The external devices may include medical imaging claims such as Video Laryngoscope, Ultrasound. The external devices may include diagnostic tools such as those made available by Point of Care labs.

The second data processor allows both the defibrillator to be maintained with updated network data and software and the one or more external devices to be maintained with updated defibrillator data. Independent controllers provide multiple processing paths on critical charge and monitoring and diagnostic capability, interventional treatment capability, and coaching functions.

Figure 4:
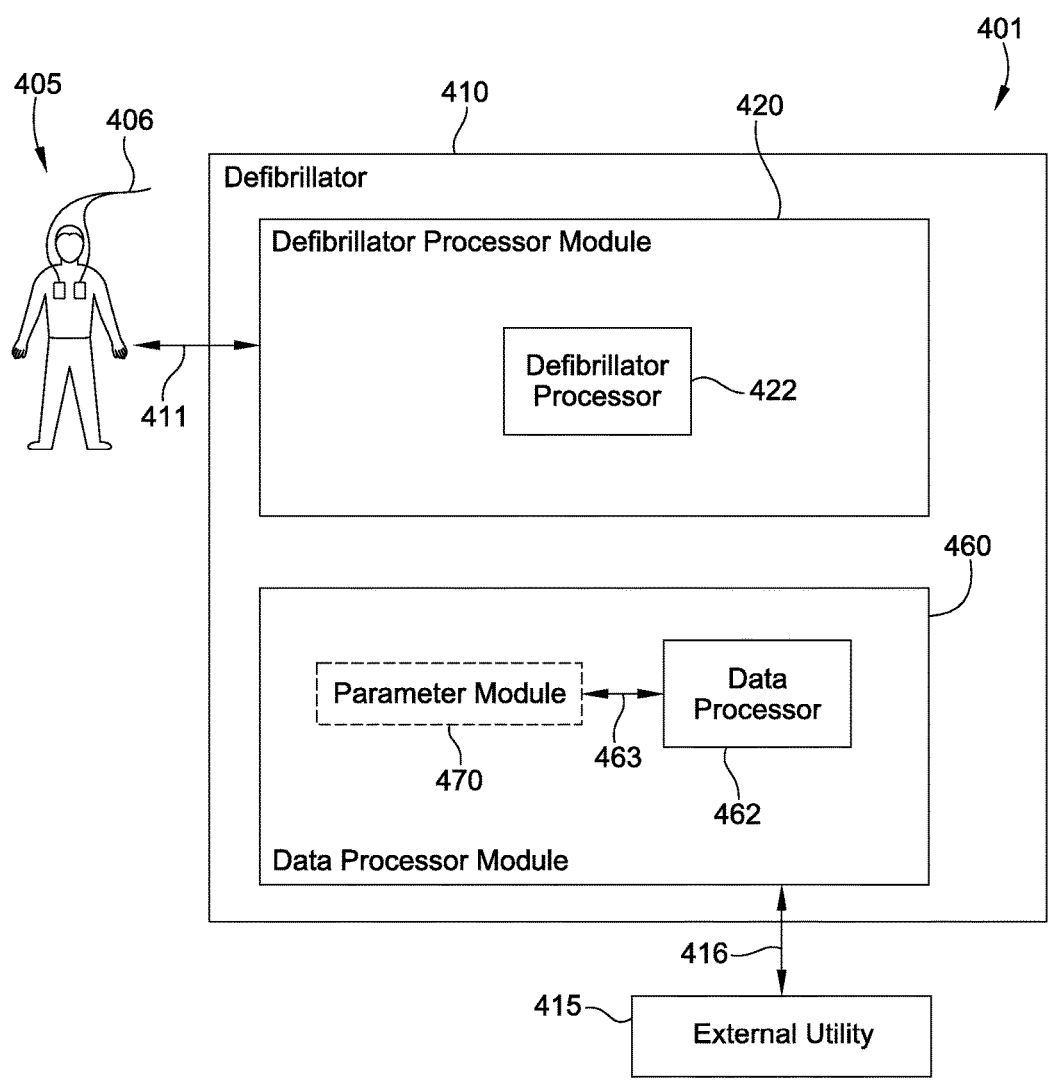
FIG. 4 shows a functional diagram of an illustrative dual processor defibrillator system of this disclosure.

FIG. 4 shows a functional diagram of an illustrative dual processor defibrillator system 401 of this disclosure. The defibrillator system comprises a defibrillator 410, a defibrillation site 405, and an external utility 415.

The defibrillation site 405 is a subject being administered a defibrillator charge through contact electrode pair 406 by a caregiver. The electrode pair (electrodes 104, 108 in FIG. 1) is attached to the skin of a person on one end. The electrode pair is tethered by hard-wiring to the defibrillator 410 for the defibrillator to administer, via the electrodes a brief, strong electric pulse through the body of the person. The pulse also known as a defibrillation shock, also goes through the heart, in an attempt to restart it, for saving the life of the person.

The defibrillation site may also be provided with an electrocardiogram (ECG) or other medical tool that is interfaced to the defibrillator for providing the defibrillator processor with patient parameter data for use by the defibrillator in controlling the defibrillation shock. For example, the ECG typically includes a set of electrodes adapted for monitoring the ECG of a patient. For example, in the standard 12 ECG lead system, the ECG leads are divided into limb leads, called—I, II, III, aVR, aVL and aVF—and precordial (chest) leads called—V1, V2, V3, V4, V5, V6. The ECG voltage potential between pairs of electrodes can be measured and recorded. The graphical display of these currents is known as an electrocardiogram, which is often referred to as an ECG. The ECG data may provide the defibrillator processor with valuable information for use in managing the defibrillatiron charge. For example, the ECG data may be displayed by the defibrillator processor on a display and is useful in revealing the condition of the heart and to diagnosis heart ailments or disease.

The defibrillator 410 comprises a defibrillator processor module 420 and a data processor module 460. The defibrillator processor module includes a defibrillator processor 422 advantageously dedicated to controlling when an electrical charge is applied to a patient as described in great detail below. The data processor module 460 comprises a data processor 462 advantageously dedicated to managing the data operations in the defibrillator for enhancing the monitoring and diagnostic capability, interventional treatment capability, and coaching of the defibrillator process as described in greater detail below. The data processor 462 may be in communication with an external utility which may be one or more external devices 415 for the bidirectional transmission and receipt of data between the data processor module and the external utility for further enhancing the coaching process. The data processor 462 may also be in communication with data residing in the defibrillator 410. The data may be data managed by the defibrillator processor 422. The data may also include data generated by a parameter module 470 described in greater detail in FIG. 6 below. The data may be any data that resides in or is generated by the defibrillator. 410. The data processor 462 allows the defibrillator 410 to be maintained with updated network data and software and allows the one or more external devices to be updated with defibrillator data. The use of independent controllers to manage the defibrillation charge and data operations of defibrillator advantageously provide multiple processing paths on critical charge and monitoring and diagnostic capability, interventional treatment capability, and coaching functions.

The external utility 415 is one or more programmed computers that may be connected to the defibrillator 410 wirelessly or by wired connection in order to allow for the exchange of information between the defibrillator and the external utility. The external utility of this disclosure may be a server. A server may be any computer configured to serve the requests of client programs running on the same or other computers on a network. In FIG. 4, the computer of the external utility may be a host computer configured to serve the requests of one or more client programs residing in the defibrillator 410. Alternatively, the computer of the external utility may serve a client residing on the external utility or on some other computer to which the external utility may be connected. Depending on the computing service that the server is configured to offer, the server may include one or more of a file server for storing and making files accessible for reading and writing to the client, a print server that manages one or more printers, a network server that manages network traffic, a mail server that manages mail on a network, a database server that allows clients to interact with a database, and/or a hospital server for managing hospital records. The server may also be in communication with one or more other servers that themselves may include one or more of the foregoing or other servers.

The external computing device may be a personal computer, a laptop computer, a tablet, a mobile computing device, or a server. The external utilities may include an adjunct medical device which may be a programmed computer that provides tools for monitoring the technique of a rescuer during the defibrillation process, such as applying CPR or proper positioning of the electrodes for application of a defibrillation charge on the patient. Illustratively, the device may monitor CPR chest compressions provided before or after defibrillation shock. For example, the device may measure the depth of a CPR chest compression, compare it to what it should be, and provide feedback to the user by way of instructions to go faster, deeper, etc. Alternatively, the adjunct medical device may be any other device that monitors defibrillation techniques and provides feedback to a rescuer at the site of the defibrillation.

Utility applications may also include existing applications that may be one or more software applications running on one or more computing devices external to the data processor module for performing a dedicated function. Examples of such functions include: performing specific services or tests.

Figure 5:
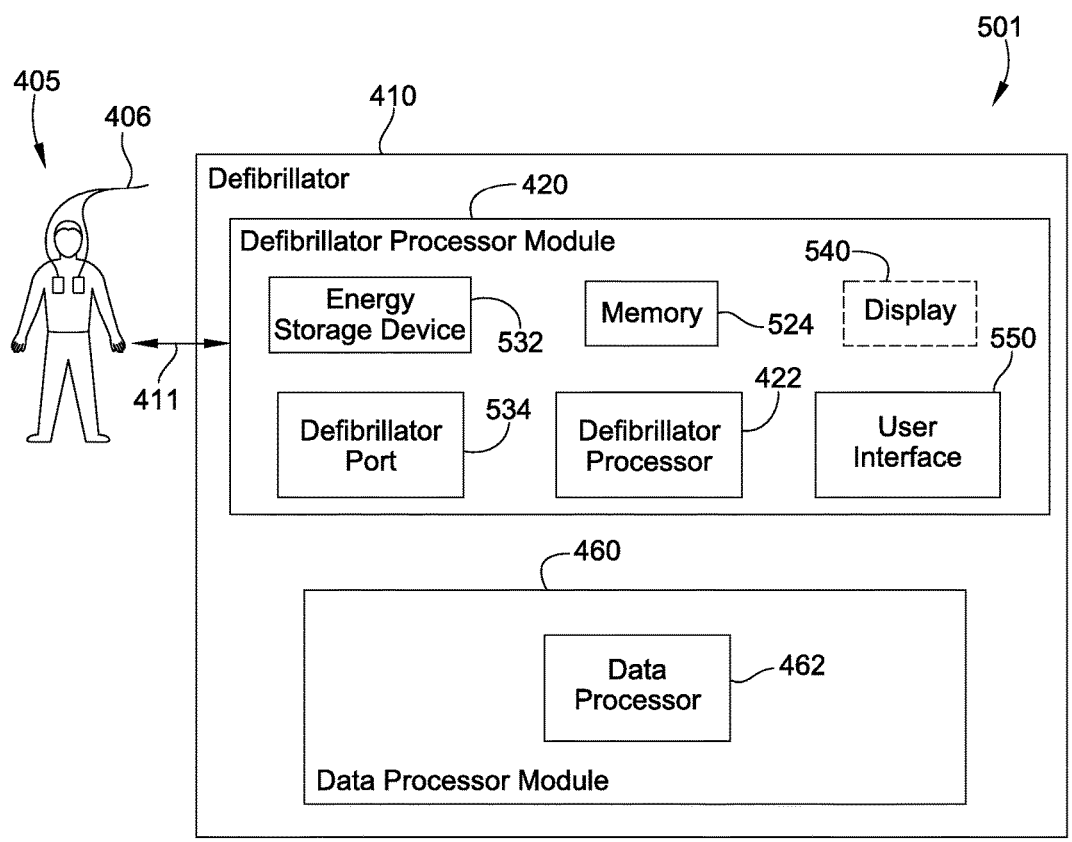
FIG. 5 is an enlarged view of the defibrillator processor module included in the defibrillator of the defibrillator system in FIG. 4.

FIG. 5 shows an enlarged view of the defibrillator processor module 420 included in the defibrillator of the defibrillator system in FIG. 4. In addition to the defibrillator processor 422, the defibrillator process module 420 further includes an energy storage device 532, a defibrillation port 534, a memory unit 524, a user interface 550, and a display 540. The display is shown in phantom since a display may be an optional feature of defibrillator 410. For example, a defibrillator with a display may enable displaying of ECG or other patient parameter data taken by medical tools interfaced to the defibrillator processor module at the defibrillation site 405.

The energy storage device 532, the defibrillation port 534, and the user interface 550 have been previously described in connection with elements 350, 310/319, and 370, respectively in FIG. 3 and that description is applicable to the description of these elements shown in FIG. 5.

The defibrillator processor 422 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The memory unit 524 of defibrillator processor module 460 can be any form of data storage device. It may be at least one of random access memory (RAM) and/or read only memory (ROM). Information can be stored permanently until overwritten and/or stored temporarily for use while the unit is active.

The display 540 of the defibrillator processor module 420 may be a visual display capable of displaying data transmitted from defibrillator processor 435. Displays for use with this disclosure may include an LCD screen, an e-paper display, or other bi-stable display, a CRT display or any other type of visual display.

Figure 6:
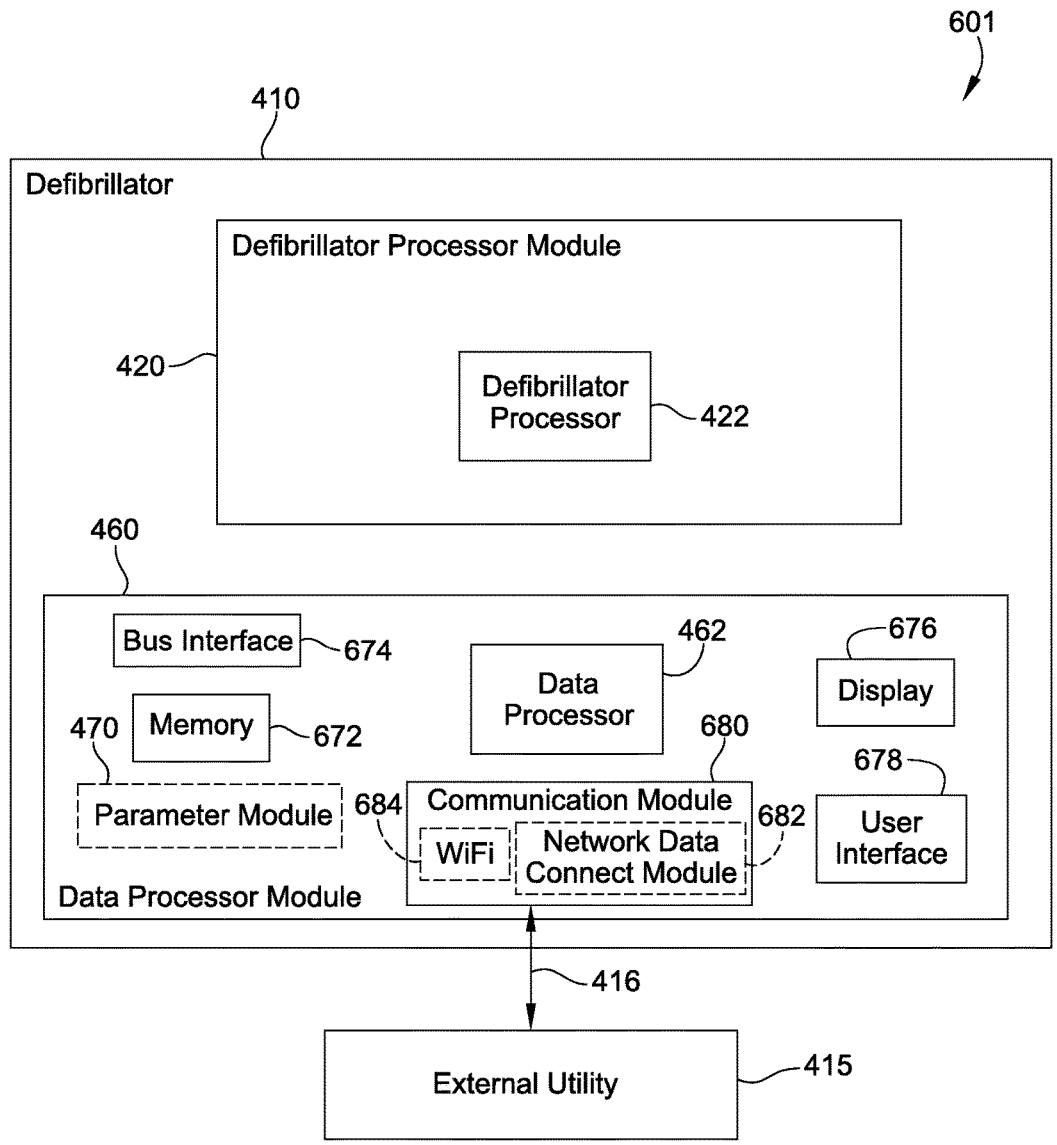
FIG. 6 is an enlarged view of the data processor module included in the defibrillator of the defibrillator system shown in FIG. 4.

FIG. 6 is an enlarged view of the Data Processor Module 460 included in the defibrillator 410 of the defibrillator system shown in FIG. 4. As previously described, the data processor module 460 includes the data processor 462 and the parameter module 470. The data processor module 460 further comprises a memory unit 672, a bus interface 674, a display 676, a user interface 678, and a communication module 680.

The data processor 460 of the data processor 460 is a general purpose central processing unit (CPU) of a personal computer (PC) that includes a PC operating system such as Microsoft's windows 8 embedded, or a version of Googles Android software. Examples of CPU's include an ARM A9 or A11, Atom, Pentium, Athlon, or other CPU. The data processor accesses instructions defined by the operating system that are stored in the memory 672, performs actions based on those instructions using data stored in the memory 672 or some other source, stores data in memory 672, transmits data from the defibrillator 410 to the one or more external utility 415. For example, the data processor 460 may send data from parameter module 470 to the external utility as discussed later in this disclosure. The data processor 462 may be configured to control modules within the defibrillator. For example, where a parameter module is included in the defibrillator, the data processor 462 may be configured to control the parameter module 470. In an alternative embodiment, where a communication module is included in the defibrillator 410, the data processor 462 may be configured to control the communication module 680. The data processor 462 may also be configured to control other data generating or data processing functionality that may be included in the defibrillator. In an illustrative embodiment, the data processor 462 controls the defibrillator processor 422 in a master slave relationship as described in greater detail below. While FIG. 6 shows a data processor 462 as a single processor, it will be appreciated that more than one processor may also be used for module processor 480 in accordance with this disclosure.

Illustratively, the data processor module resides inside the defibrillator. Alternatively, the data processor module may reside in a self contained package unit that is physically attached to the outside of the defibrillator. The data processor may also reside in a device that is separate from the defibrillator. In this embodiment, the separate device is likewise provided with a communication module that is compatible with the communication module of the defibrillator as required to establish the communication link with the defibrillator. The separate device may further provide accessory solutions to the defibrillator. For example, the separate device may be configured, for example, to provide audio, video, or audio-visual coaching and/or to serve as a data collection tool in support of the treatment of a patient with the defibrillator.

Whereas the defibrillator processor module is configured to provide operations considered essential for the survival of the patient, the data processor module may be configured to provide operations not considered essential for the survival of the patient. Non-survival essential operations may illustratively include tasks that do not impair the ability of the defibrillator processor module to deliver electrical charge. Non-survival essential operations may also include coaching operations such as extended monitoring, extended diagnosis, and interventional treatments. Illustratively, the communication and control of the data processor module may be configured so that it does not negatively affect the ability of the defibrillator processor module to perform it's essential function of delivering electrical charge to the patient. In other words, communication and control of the data processor module is configured to avoid interfering with the defibrillator processor module control of the electrical charge applied.

The parameter module 470 may be any monitor configured to detect a parameter of a patient. The patient parameter may include one or more of the following measurements: a measurement of $C_{O2}$ exhaled by a patient; an electrical activity of the heart of a patient; an exchange of air between the lungs of a patient and the atmosphere; a pressure of the blood in a patient; a temperature of a patient; an oxygen saturation in the blood of a patient; a chest compression of a patient; an image of the internal structure of a patient; an oxygen saturation in the blood in the brain of a patient; the acidity or alkalinity of fluids in a patient; or other patient parameter.

The patient parameter of the $CO_2$ exhaled by a patient may be measured using capnography techniques. The patient parameter of the electrical activity of the heart of a patient may be measured using ECG techniques. The patient parameter of the exchange of air between the lungs of a patient and the atmosphere may be measured using ventilation techniques. The patient parameter of the measurement of the pressure of the blood in a patient may be measured using non-invasive blood pressure measurement techniques or invasive blood pressure measurement techniques. The patient parameter of the temperature of a patient may be measured using temperature measurement techniques. The patient parameter of the oxygen saturation in the blood of a patient may be measured using pulse oximeter techniques or tissue oximetry techniques. The patient parameter of the chest compression of a patient may be measured using chest compression detection and feedback techniques. The patient parameter of the image of the internal structure of a patient may be measured using ultrasound measurement techniques. The patient parameter of the oxygen saturation in the blood in the brain of a patient may be measured using cerebral oximetry techniques. The patient parameter of the acidity or alkalinity of fluids in a patient may be measured using non-invasive pH measurement techniques. These and other techniques and modules for generating the foregoing and other kind of patient parameter data for use with this disclosure are well known in the art.

The memory unit 672 of data processor module 460 can be any form of data storage device. It may be at least one of random access memory (RAM) and/or read only memory (ROM). Information can be stored permanently until overwritten and/or stored temporarily for use while the unit is active.

The bus interface 674 may be any hardware or software contruct that allows the exchange of data between the data processor 462, the memory 672, the parameter module 470, the display 676, the user interface 678, the communication module 680, and any other modules or components residing inside the data processor module.

The display 676 of the data of the data processor module may be a visual display capable of displaying data transmitted from defibrillator processor 435. Displays for use with this disclosure may include an LCD screen, an e-paper display, or other bi-stable display, a CRT display or any other type of visual display.

The user interface 678 of the data processor module can be implemented in any number of ways. For example, the user interface 678 may include a screen, to display a parameter of a patient that is detected and measured, provide visual feedback to the rescuer for their resuscitation attempts, and so on. Interface 678 may also include a speaker, to issue voice prompts, etc. Interface 678 may additionally include various controls, such as pushbuttons, keyboards, and so on. The user interface may allow the user to enter data and instructions to the defibrillator 410 to select applications for the data processor to execute, select features of the defibrillator to operate, to, set settings, preferences, rules, etc; and generally to adapt the configuration of the defibrillator 410 to a particular application and user.

Communication module 680 is hardware and software configured to transmit data to and from the defibrillator 410. Illustratively, the communication module 680 is configured to transmit data from the defibrillator to the external utility 415. The external utility 415 may be a wireless patient monitor, computer, a laptop, a server, a mobile computing device, or other computing device. Alternatively, the data processor 462 may receive data from the external utility through the communication module 680 to the defibrillator 410. Hence, communication module 680 provides for the bidirectional transmission of data between the defibrillator 410 and the external utility 415. In order to allow for the bidirectional flow of data between the defibrillator and the external utility, the external utility is likewise provided with a communication module (not shown) that is compatible with the communication module 680 as required to establish the communication link with the communication module 680 of the data processor module 460. Together, the communication module 680 of the data processor module 460 and the external utility 415, respectively, enable a communication link 416 to be established between the data processor module 460, and hence the defibrillator 410, and the external utility 415 for enabling the bidirectional flow of data between the defibrillator and external utility devices.

In an illustrative embodiment, the communication module 680 may include a wireless module 684 and/or a network data connect module 492 as shown in FIG. 6. The wireless module may illustratively be a Wi-Fi module. Alternatively, the wireless module 684 may be a blue tooth module, a CDMA module, or any other communication module that enables a wireless communication link for the bidirectional flow of data between devices wirelessly. For example the wireless module may be based on a protocol such as cellular, Wi-Fi, Ultra Wideband, NFC, Ethernet, Bluetooth, and ZigBee, etc. The network data connect module 682 may be a hardware and software based data connector configured to connect with a data outlet of the external utility 416. The network data connect module 682 may be one or more ports and associated circuitry and software that allow bidirectional flow of data between the data processor module 460 and the external utility 415. Illustratively, the network data connect module is an Ethernet connector configured for connection to the external utility 682 in a wired connection. Alternatively, the network data connect module may be an RS232 connector, a USB or other wire connector. For example, the data network data connect module may be based on a protocol take from the group of protocols consisting of SPI and USB. Other connectors and hardware and software configurable for providing a wired connection between the communication module 680 and the external utility 415 may be used for network data connect module 682 as are well known in the art.

Figure 7:
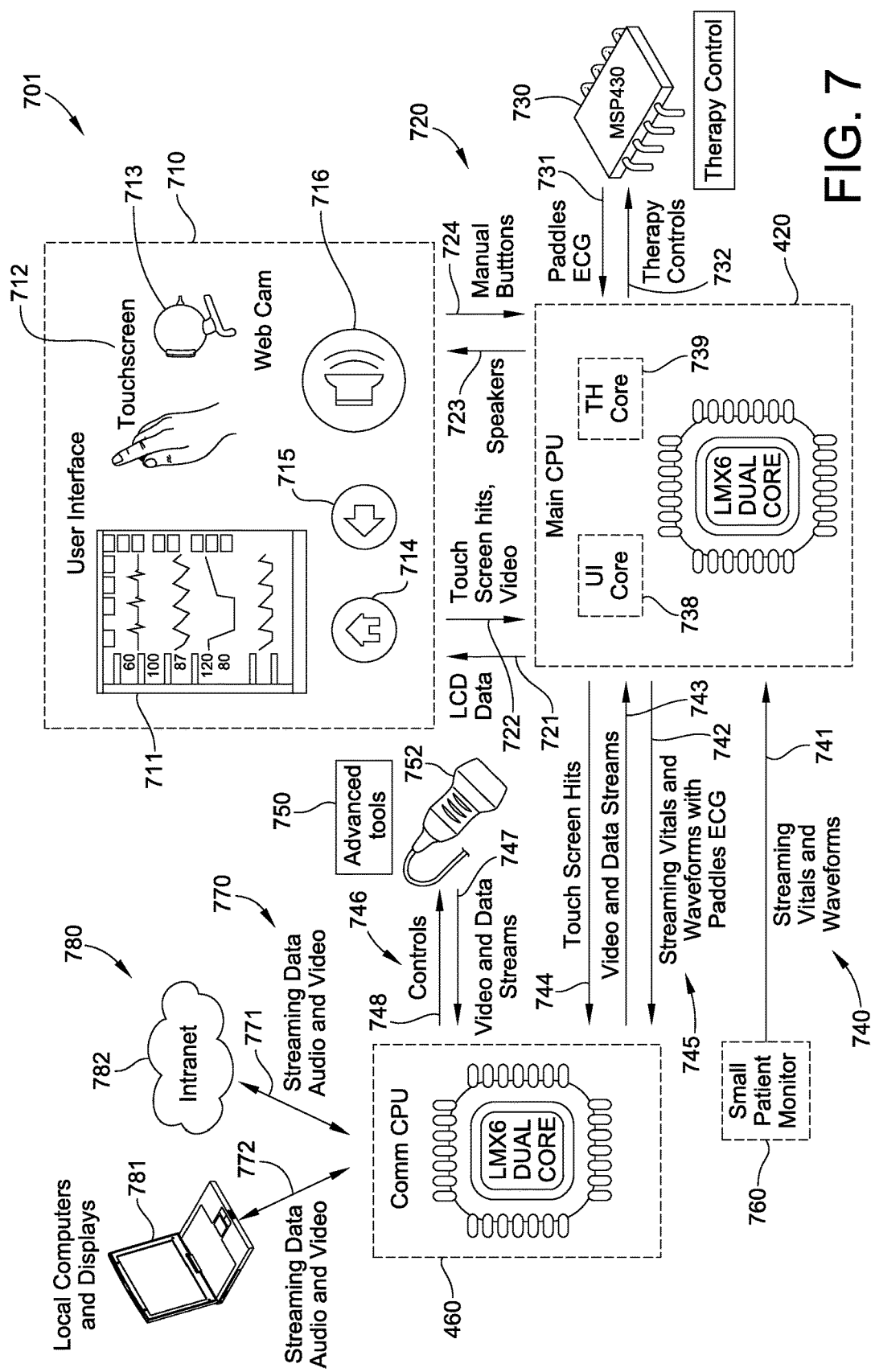
FIG. 7 shows an illustrative embodiment of the dual processor defibrillator system of this disclosure.

FIG. 7 shows an illustrative embodiment of the dual processor defibrillator system 701 of this disclosure. Dual processor defibrillator system 701 includes a user interface 710, a data processor module 460, a defibrillator processor module 420, a therapy controller 730, a small patient monitor 760, advanced tools 750, and network resources 780.

Data processor module 460 is illustratively an i.MX6 Dual Core processor manufactured by Freescale. The i.MX processor offers a versatile platform for multimedia and display applications. Alternatively, the data processor module may be any data processor with processing capability sufficient to execute the data processing operations of the defibrillator described in this disclosure or as will be apparent to one skilled in the art based on this disclosure.

Defibrillator processor module 420 is illustratively also an i.MX6 Dual Core processor manufactured by Freescale. Alternatively, data processor module may be any data processor with processing capability sufficient to execute the data processing operations of the defibrillator. Alternatively, the defibrillator processor module may be any processor with processing capability sufficient to execute the defibrillator processing operations of the defibrillator described in this disclosure or as will be apparent to one skilled in the art based on this disclosure. Illustratively, one of the cores 739 of the i.MX6 Dual Core processor is dedicated to controlling the therapy control module 730. The other core 738 of the i.MX6 Dual Core processor is dedicated to controlling the interface of the defibrillator processor module to the data processor module 460, the user interface 710, to external devices, such as the small patient monitor 760, and/or to other components internal or external to the defibrillator.

User interface 710 illustrative includes a screen 711 to display a parameter of a patient that is detected and measured, provide visual feedback to the rescuer for their resuscitation attempts, and so on. Interface 710 further includes a touch screen 712 as part of or separate from the display screen that is responsive to the touch of a user. For example, the touch screen may display a virtual keyboard and/or a menu for a user to enter data and/or to navigate through the menu and to execute different menu activatable events. The user interface 710 also illustratively includes a speaker 716, to issue voice prompts, etc. Interface 710 may additionally include various controls, such as pushbuttons, 714, 715, keyboards, and so on. In addition, the user interface 710 enables a user to control the defibrillator processor module 420.

Therapy controller 730 is a hardware and software module configured to control ECG data and the application of an electric shock to the patient. The defibrillator processor module executes the software that provides control signals 731 for the control of ECG data and control signals 732 for the control of the electric shock applied to the patient.

As indicated, the core 738 of the i.MX6 Dual Core processor is dedicated to controlling the interface of the defibrillator processor module to the data processor module 460, the user interface 710, to external devices, such as the small patient monitor 760, and/or to other components internal or external to the defibrillator. The small patient monitor may be a small monitor external to the defibrillator that may be connected to the defibrillator in order to make a second display screen available to the caregiver to expand the display capability that is made possible by the display screen 711 that is integral to the defibrillator.

Figure 8:
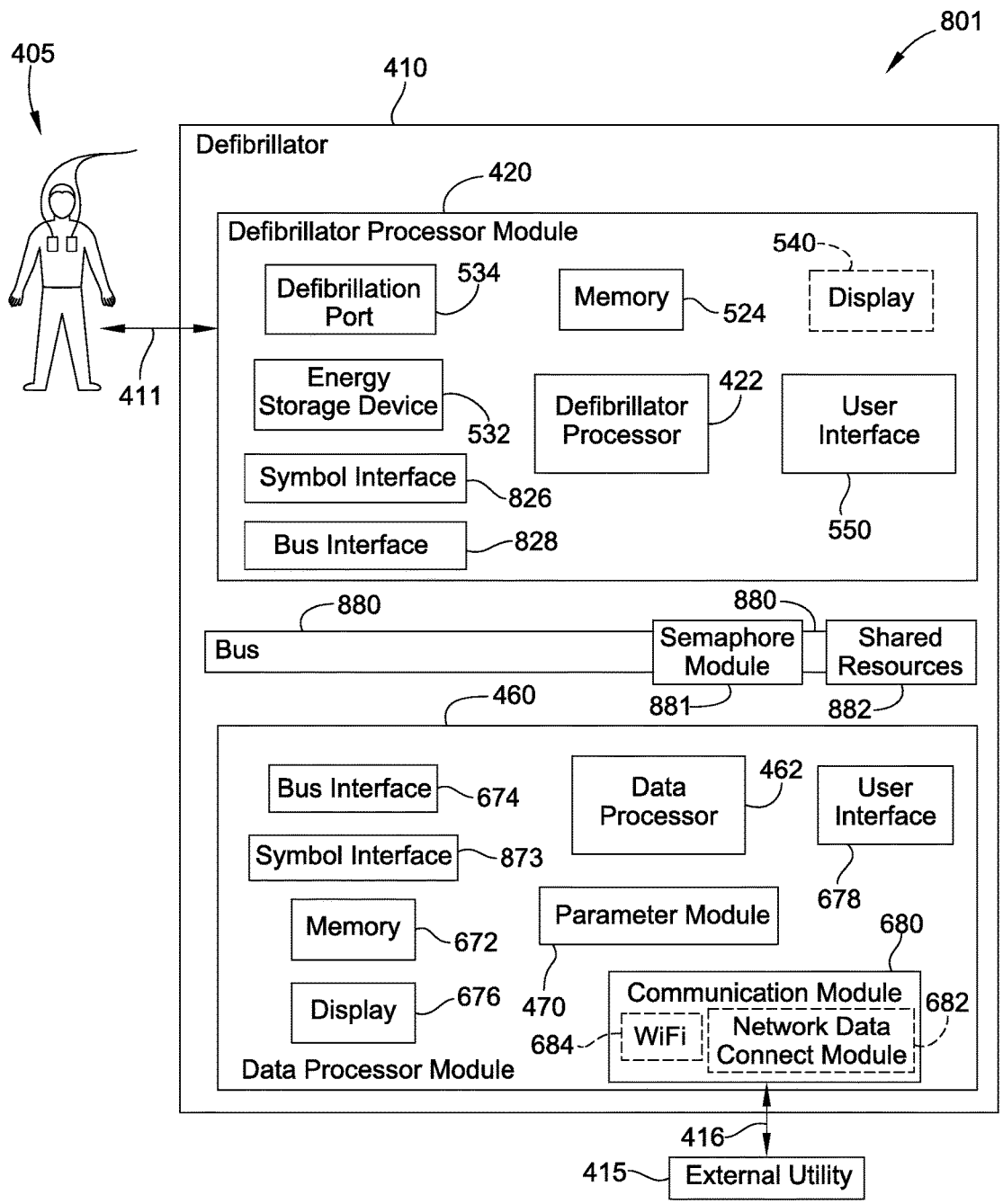
FIG. 8 shows an illustrative embodiment of another defibrillator system of this disclosure employing the dual processor defibrillator of FIG. 4.
Figure 9:
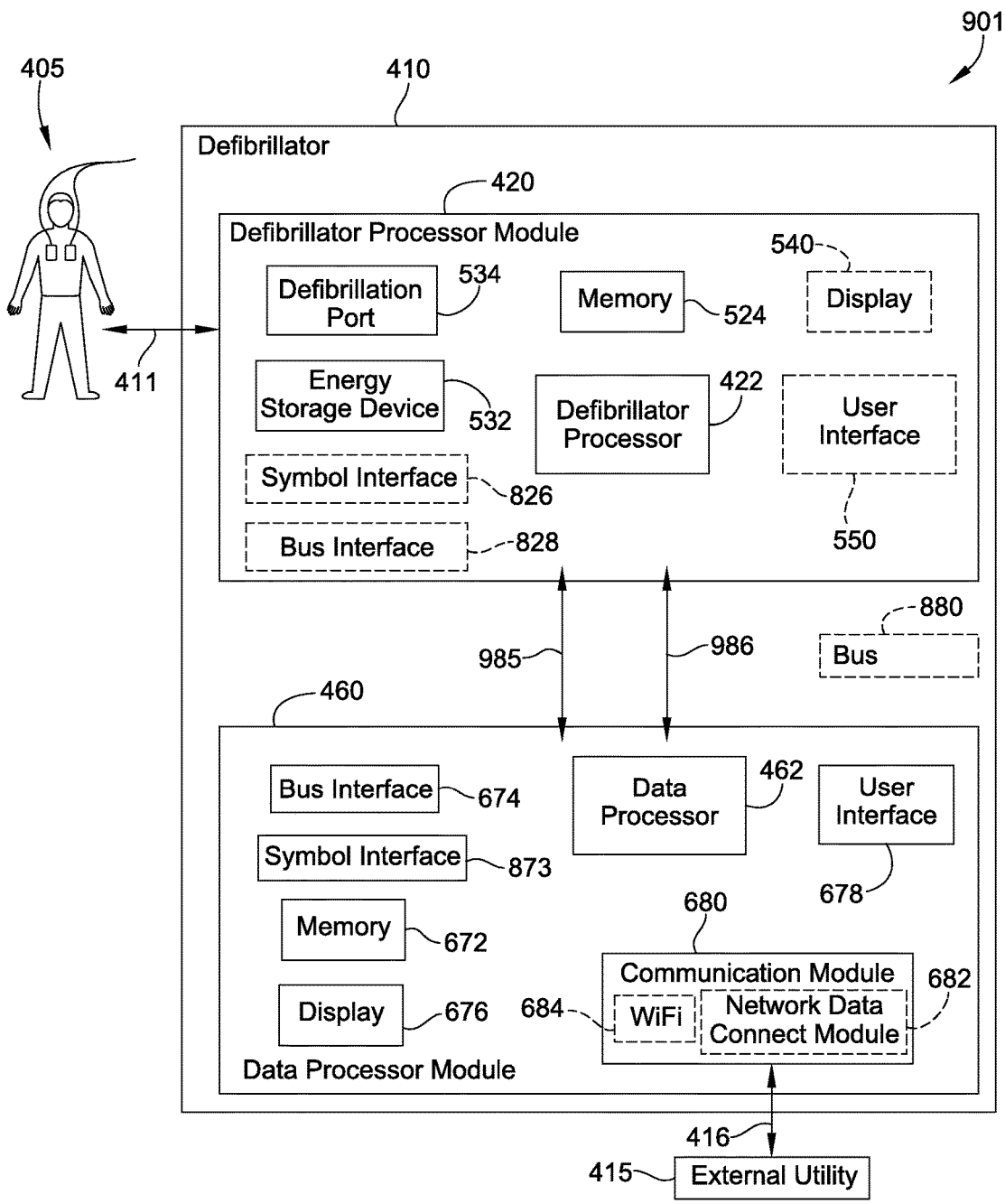
FIG. 9 shows an illustrative embodiment of another defibrillator system of this disclosure employing the dual processor defibrillator of FIG. 4.
Figure 10:
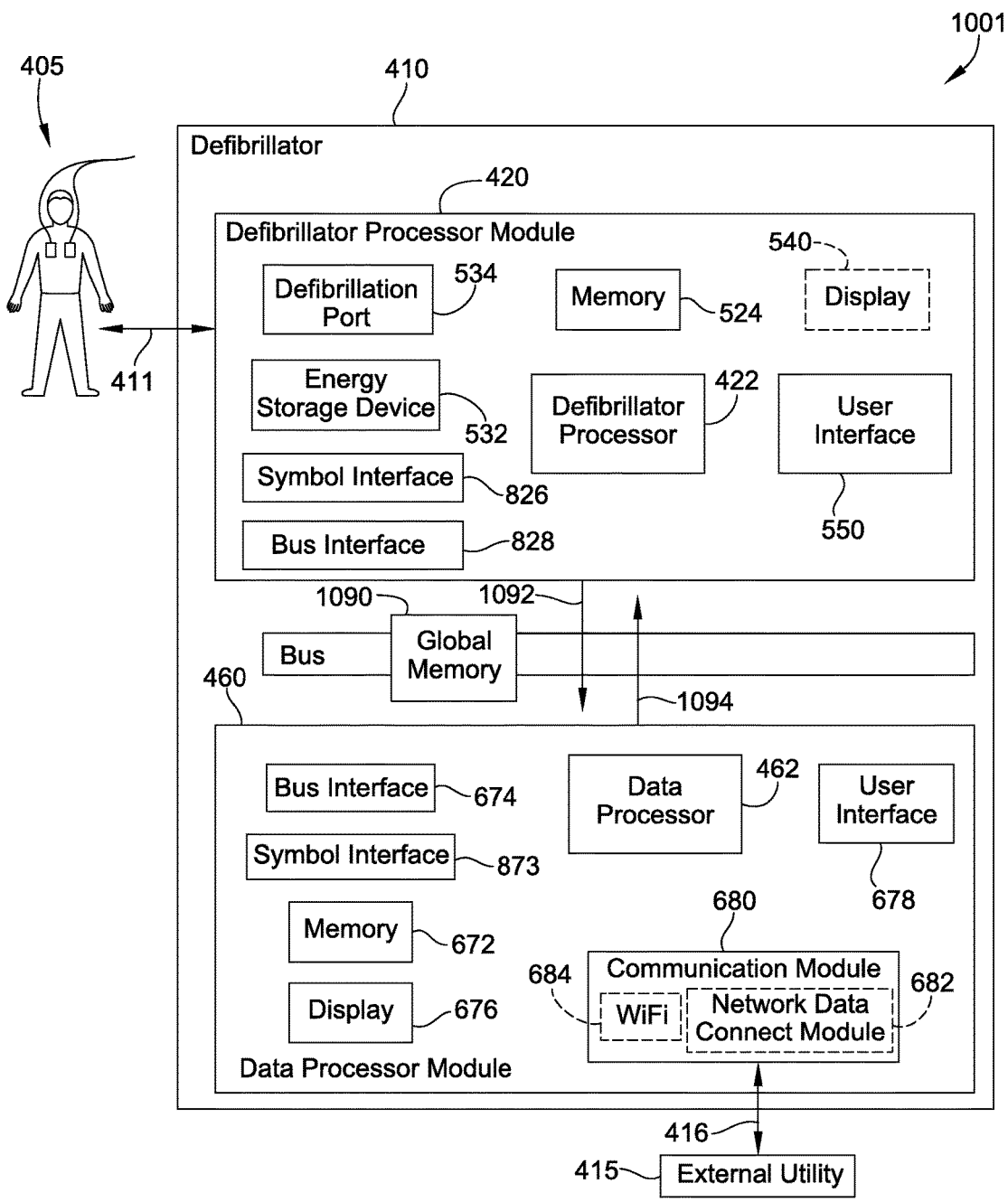
FIG. 10 shows an illustrative embodiment of another defibrillator system of this disclosure employing the dual processor defibrillator of FIG. 4.

As shown in FIG. 7, the defibrillator processor module executes the software that provides control signals 741 for controlling the data generated by the small patient monitor such as vitals data and waveform data that may be streamed from the small patient monitor. As also shown, the defibrillator processor module executes the software that provides control signals 745 of data that may pass between the defibrillator processor module 420 and the data processor module 460. In the illustrative example shown in FIG. 7, cross-talk 745 between the i.MX6 Dual Core processor of the defibrillator processor module and the i.MX6 Dual Core processor of the data processor module occurs in accordance with protocols defined by the architecture of the i.MX6 Dual Core processor. In alternative embodiments, the processors of the defibrillator processor module and the data processor module may be configured to communicate with each other using architecture as illustrated in FIGS. 8-10 described below, or in other ways known to those skilled in the art.

As shown in FIG. 7, the cross-talk 745 between the i.MX6 Dual Core processor of the defibrillator processor module and the i.MX6 Dual Core processor of the data processor module may include control signals 742 for the transmission of vital and waveform data and streams which may include ECG data to the data processor module. The cross-talk 745 may also include control signals 744 for the transmission of data detected by the touch screen 712 of the user interface 710. This data may be used by the data processor module in performing data operations as described in this disclosure. The cross-talk 745 may further include control signals 743 for controlling data stream transmissions from the data processor module 460 to the defibrillator processor module 420. For example, the data processor module may transmit video and data streams generated or managed by the data processor module to the defibrillator processor module for display on the display screen 711 of the user interface 710.

The cross-talk may be used to control power management of one processor by the other. As one example, the cross-talk may be used to control power management by the defibrillator processor of the data processor or to control power management by the data processor of the defibrillator processor. The cross-talk may be used to control power management by the defibrillator processor of the external devices connected to the data processor or to control power management by the data processor of the external devices connected to the defibrillator processor.

Advantageously, the design and layout of the defibrillator processor module and the data processor module is done in a way that critical operations on the defibrillator process are isolated from data processor failures. This ensures that the defibrillator processor is isolated in its processing from the processing done by the data processor so that any safety critical function on the defibrillator processor are less likely to fail due to a failure in the data processor.

The data processor module 460 also controls other data operations as explained in this disclosure. As shown in FIG. 7, the data processor module controls advanced tools 752 that may be electrically connected to the data processor module through the communication module of the defibrillator. Illustrative advanced tools may include a laryngoscope, an ultrasound wand, and so on. The data processor module provides control signals 748 for controlling these advanced tools. The data processor module also controls the receipt of video and data streams from the advanced tools over communication line 747 in response to the control signals 748.

The data processor module also provides control signals 770 for the steaming 772 of data, audio and video data from local computers 781, displays, and other external resources as further explained below. The data processor module also provides control signals 770 for the streaming 771 of data, audio and video data from remote computers 780, displays, and other external resources as also further explained below.

FIG. 8 shows an illustrative embodiment of another defibrillator system 801 of this disclosure employing the dual processor defibrillator of FIG. 4. Defibrillator 410 comprises a defibrillator processor module 420, a data processor module 460, a semaphore module 781, shared resources 782, and a bus 780.

The defibrillator processor module 420 includes the defibrillator processor 422 of FIG. 4, the memory 524 of FIG. 5, the defibrillation port 534 of FIG. 5, the energy storage device 532 of FIG. 5, the display 540 of FIG. 5, and the user interface 550 of FIG. 5. These elements have been previously described in connection with FIG. 5 and the description of those elements is applicable to the description of these elements shown in FIG. 8. In the FIG. 8 embodiment, the defibrillator processor module further includes a symbol interface 826, and a bus interface 828.

The symbol interface 826 may be any hardware or software construct that allows the synchronization of the exchange of data between elements residing within the defibrillator processor module 420 and the shared resources 882. More specifically, the symbol interface allows the synchronization of the exchange of data between the defibrillator processor 422, the memory 524, the display 540, the user interface 550, and the defibrillation port 534, any other modules or components residing in the defibrillator processor module and shared resources 882. The symbol interface 826 allows coordination and synchronization of data flow both from within the defibrillator processor module and outside the data processor module with the shared resources 882.

The bus interface 828 may be any hardware or software construct that allows the exchange of data between the defibrillator processor 422, the memory 524, the display 540, the user interface 550, the defibrillation port 534, any other modules or components residing in the defibrillator processor module 420, and the shared resources 882.

The data processor module 460 includes the data processor 462 of FIG. 6, the memory 672 of FIG. 6, the parameter module 470 of FIG. 4, the display 676 of FIG. 6, the user interface 678 of FIG. 6, the communication module 680 of FIG. 6. These elements have been previously described in connection with FIG. 6 and the description of those elements is applicable to the description of these elements shown in FIG. 8. In the FIG. 8 embodiment, the data processor module further includes a symbol interface 873 and a bus interface 674. These elements operate in like manner to the symbol interface 826 and the bus interface 828 previously described in connection with the defibrillator processor module 420 of this FIG. 8.

The shared resources 882 is one or more resources that may be shared between the defibrillator processor 422 and the data processor 462. Illustratively, the share resource is a shared display. Alternatively, the shared resources 882 may be a plurality of displays. The shared resources 882 may be any resource that may be useful to both the defibrillator processor and the data processor. By way of example, the shared resource includes, but is not limited to a user interface, a memory unit, a module for generating data, or any other device that may be useful to both the defibrillator processor and the data processor and hence useful for sharing between the defibrillator processor module and the data processor module. An illustrative embodiment of a shared data generating device is the parameter module 470 described in FIGS. 4 and 6 which provide patent parameter data as previously described. In this embodiment, both the defibrillator processor and the data processor may access the parameter module 470 to obtain patient parameter data. In this example, the defibrillator processor may be accessing this patient parameter data for the purpose of managing the charge to apply to a patient. In the case of the data processor, the data processor may be accessing this patient parameter data for the purpose of data collection for coaching purposes.

The semaphore module 881 is a memory location for storing semaphore flags which indicate which of either the defibrillator processor 422 and the data processor 462 has acquired the respective shared resources 882. If the shared resources 882 is a single resource, there will typically be one semaphore flag associated with that resource. For example, if shared resources is a shared display, there will typically be one semaphore flag associated with the shared display. If shared resources include other resources, such as a plurality of displays; a display and a user interface; a display and a parameter module; and so on, then there will typically be one semaphore flag associated with each of these resources of the shared resources 882.

In operation, when one of either the defibrillator processor or the data processor executes an instruction to access the shared resources 882, the acquiring processor performs a read-modify-write action on the flag in the semaphore module 881 to acquire the shared resources 882. By reading a flag that is not currently being read by the other processor, the acquiring processor may modify or set the flag to indicate that the acquiring processor has take control of that flag and hence the shared resources. The acquiring processor can then execute write instructions to address the shared resources and to instruct the shared resources. By the use of read-modify-write actions, either processor is enabled to take over control of the semaphore module 881 and controlling the shared resources for so long as the acquiring processor is controlling the shared resources.

Once the acquiring processor has successfully set a flag it proceeds to execute subsequent instructions from its associated memory which may include write instructions to address corresponding to locations of the shared resources 882 sought to be used by the acquiring processor and to instruct the shared resources 882 to perform some function. Following those instructions, the acquiring processor executes a release instruction specifying release of the shared resources 882. In response to this instruction the flag for the shared resources 882 is cleared so that either of the defibrillator processor or data processor may successfully acquire use of the shared resources 882 by read-modify-write action on the flag.

It will be appreciated that the inter processor interface bus 880 may include a message based communication link. In addition, the semaphore module may be configured for enabling coordinated access to the shared resource by the defibrillator processor module and the data processor module.

FIGS. 9 and 10 show illustrative interprocess communication (IPC) for allowing coordination of activities between the different program processes that are running concurrently on the defibrillator processor module and the data processor module in the operating system defined by the defibrillator 410. Generally, an IPC includes thread synchronization and data exchange between threads of each processor beyond its process boundaries. IPC methods include pipes and named pipes (FIFO); streams and messages, message queuing; semaphores; shared memory, sockets, transport level interface, etc. Each has its own advantages and limitations and the defibrillator 410 may use more than one IPC in coordinating communications between the processors.

In one illustrative IPC shown in FIG. 9 a defibrillator 410 comprises a defibrillator processor module 420, a data processor module 460, a control signal line 986 and an interprocessor communication unit 985.

The defibrillator processor module 420 and the data processor module 460 comprise the same elements previously described in connection with FIG. 8 and the description of those elements is applicable to the description of these elements shown in FIG. 9. Interprocessor communication unit 985 is illustratively a bus that allows the transfer of data between the defibrillator processor 422 and the data processor 462. Illustratively, the bus may be a PCI or other type of communication bus. For example, interprocessor communication unit 985 may be an IDE bus typically used for connecting storage to a processor. In FIG. 9, the IDE bus connects the defibrillator processor to the data processor. In this way, data from the defibrillator processor may be passed over to the data processor for the data processor. The data processor may use the defibrillator data in programs that the data processor is executing to provide coaching to the caregiver. Alternatively, the data processor may transfer the defibrillator data over to the external utility 415 of the network via the communication link 416. Similarly, data from the data processor may be passed over to the defibrillator processor for use by the defibrillator processor in controlling the application of a charge to a patient.

Control signal line 986 is a hardwire line used by either processor to assert control over the other processor. In other words, control signal line 886 allows one processor to become master over the other processor which becomes the slave in a master slave relationship between the two processors. For example, if the defibrillator processor wants to pass defibrillator data over to the data processor to transfer to the network, the defibrillator processor may assert the control signal line 986 telling the data processor that it has data to pass over to the data processor. The data may then pass over the IDE bus connecting the two processors from the defibrillator processor to the data processor. In another example, if the data processor wants to pass data processor data over to the defibrillator processor, the data processor may assert the control signal line 886 telling the defibrillator processor that it has data to pass over to the defibrillator processor. The data may then pass over the IDE bus from the data processor to the defibrillator processor.

FIG. 10 shows an illustrative embodiment of another defibrillator system of this disclosure employing the dual processor defibrillator of FIG. 4. Defibrillator 410 comprises a defibrillator processor module 420, a data processor module 460, a global memory unit 1090 and control hardwires 1092 and 1094. The defibrillator processor module 420 and the data processor module 460 comprise the same elements previously described in connection with FIG. 8 and the description of those elements is applicable to the description of these elements shown in FIG. 10.

Global memory unit 1090 is a global memory device which is tightly coupled to each processor so that each processor is able to map a segment of its virtual space into an identical segment of a physical memory defined by the global memory unit. This allows each processor to put data into a memory location that is accessible by both computers.

Control hardwires 1092 and 1094 are a hardwire line used by either processor to assert control over the other processor. In particular, they allow each processor to assert a request of the other processor which the other process responds to with an acknowledge signal. As in the illustrative example in FIG. 9, control hardwires 1092 and 1094 allow one processor to become master over the other processor which becomes the slave in a master slave relationship between the two processors. For example, if the defibrillator processor wants to pass defibrillator data over to the data processor to transfer to the network, the defibrillator processor may store the data to be transferred into the global memory and then assert a request over one of the control hardwires. The data processor responds with an acknowledge over the other control hardwire, which completes the handshake between the two processors after which the data processor may access the data stored by the defibrillator processor in the global memory. In another example, if the data processor wants to pass data processor data over to the defibrillator processor for the defibrillator processor to use in applying a charge, the data processor may store the data to be transferred into the global memory and then assert a request over one of the control hardwires. The defibrillator processor responds with an acknowledge over the other control hardwire, which completes the handshake between the two processors after which the defibrillator processor may access the data stored by the data processor in the global memory and then use that data in managing the process of applying the charge to the patient.

To operate the defibrillator shown in FIGS. 4-10, the defibrillator is first powered on. Once powered on, the defibrillator processor engages in executing a set of instructions residing in memory associated with a first set of applications directed to controlling the charging of the energy storage device and when to apply the charge to the patient As part of this control process, the defibrillator processor may also be configured to monitor the electrocardiogram (ECG) of the patient. At the same time, but by an independent computing system, the data processor engages in executing instructions of the PS operating system and specific applications of that PC operating system residing in memory 672. For example, one application may enable the operation of the parameter module to generate one or more patient parameter data. The data processor may execute the instructions that specify which patient parameters to generate and to turn on the parameter module for that purpose. As another example, the data processor may enable the operation of the communication module in order to establish a communication link with one or more external utilities. As yet another example, the data processor may execute instructions in other applications residing in memory 672 for the purpose of generating data, accessing data residing on the defibrillator, etc. in order to collect, aggregate, and correlate data for use in coaching the caregiver.

Further, there may be other data that the data processor module may generate internally or receive from external devices and the data processor module may deliver a variety of coaching to the caregiver in a number of way. For example, this data as well as coaching information from external resources is immediately available to a rescuer for use in the defibrillation. The coaching information can be made immediately available by display on the defibrillator display as indicated in the previous example. Alternatively, it may be made available in other ways, such as by triggering audible or visual data streams to assist in the defibrillation process. For example, the disclosed data processor module may enable a live video or audio stream to be fed to the display in order to provide live or delayed audio or video to coach the rescuer through a defibrillation process, whether it be for coaching relating to setting or applying the charge to the patient, to the mechanics of CPR techniques that may be used in the process, or to other aspects of a defibrillation. The video feed from the external device may include a video stream generated by an external device such as a laryngoscope or an ultrasound wand. In another illustrative embodiment, the data processor module may display the video feed from the external device on the display of the data processor module display different coaching information on the display of the defibrillator processor module. As yet another example, the disclosed data processing module may trigger audible or visual alerts on the defibrillator when the defibrillation process moves close to or outside an operating envelope that has been defined for operation of the defibrillator. The coaching made possible by this disclosure includes extended monitoring, extended diagnosis, and interventional treatments.

In addition, the disclosed data processor module enables the control of the defibrillator remotely whereby a remote resource may partly or completely take over control of the defibrillator functionality that determines the defibrillation operation such as settings, such as the charge level to be applied to a patient, etc. This feature enables trained medical personnel to determine and set the proper operation, settings, etc. of the defibrillator in circumstances where the rescuer at the scene may be without the medical training to make these determinations; thereby increasing the likelihood of success of the defibrillation. As a result, defibrillator-monitors— which are intended to be used by persons in the medical profession, such as doctors, nurses, paramedics, emergency medical technicians, etc. who may be trained to provide medical treatment to the patient during a defibrillation process based upon information provided by the monitor— that are used with the disclosed data processor module may be deployed more widely. No longer is it necessary to generally limit access to such a defibrillator-monitor to trained medical professionals. With the disclosed defibrillation system, the defibrillator-monitor may be used more widely in the field. In a normal mode of operation, these defibrillator-monitors that may be widely deployed may come with the functionality requiring trained medical expertise to operate disabled so as to allow the defibrillator part of the device to be used broadly by members of the public provided they have obtained first aid and CPR/AED training, much like the broad deployment conventionally seen with an AED. In a second mode of operation, such as a monitoring mode of operation, the monitoring functionality of the defibrillator-monitor that is used with the disclosed data processor module may be enabled. In one embodiment, the enablement occurs by remote resources that can take over and use this functionality remotely. In another embodiment, the enablement may occur by a doctor or other medically trained personnel who happen to be at the site where the defibrillation is needed. In these instances, the monitoring functionality may be enabled by the trained medical personnel such as by entry of a password into a keyboard that may be provided on the defibrillator-monitor. In another example, the functionality may be enabled remotely after a network resource has validated the identity of the medical provider qualified to use the monitoring functionality. In either and other cases, the disclosed system enables more pervasive use of defibrillator-monitors in the field because of the controls on the use of the monitoring features that are provided by this disclosure.

In the above and other ways, the disclosed defibrillator system allows for a wide range of information to be made available to the user of the defibrillator to aid in the defibrillation process. The foregoing and other coaching provided by the data processor module in the defibrillator system of this disclosure thus helps a user of a defibrillator to optimize the timing and manner of applying a defibrillator charge to a patient based upon these parametric conditions. The foregoing and other coaching provided by the data processor module in the defibrillator system of this disclosure helps assist the rescuer optimize the timing and manner of applying a defibrillator charge to a patient. The data processor module in the defibrillator system of this disclosure enables external devices to better coach users of the defibrillator through data transmitted to the defibrillator through the data processor module as a proxy for the external devices. The data processor module of this disclosure may also receive data from the defibrillator during or before or after defibrillation for use by the data processor module or for transmission by the data processor module as proxy to the defibrillator processor module to external devices. The data processor module in the defibrillator system of this disclosure also helps provide defibrillators with a seamless communication link for the communication of data between the defibrillator and the one or more external devices. The data processor module in the defibrillator system of this disclosure also helps provide defibrillators with a seamless integration with one or more external devices into a system that can provide a more holistic approach to the defibrillation process and a more effective defibrillation process.

Figure 11:
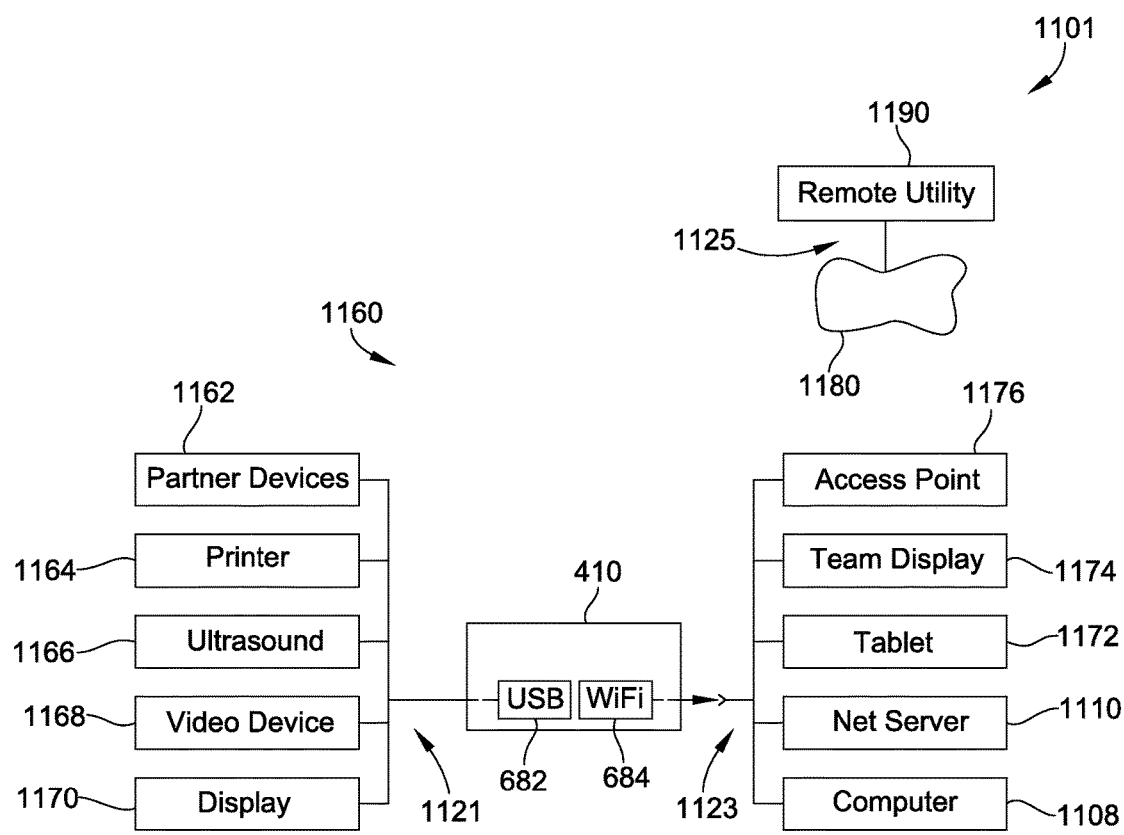
FIG. 11 shows an illustrative range of services that a network may provide in supporting the user of the defibrillator in the dual processor defibrillator system of FIG. 4.

FIG. 11 shows an illustrative range of services 1160 that the network may provide the data processor module in supporting the user of the defibrillator. FIG. 11 shows utility connect 682, which is a USB connector in this illustrative embodiment, connected with a display 1170, a video device 1168, an ultrasound device 1166, a printer 1164, and partner devices 1162. Each of display 1170, video device 1168, ultrasound 1160, printer 1164, and partner devices 1162 provide an additional service to the data processor module. For example, the video device 1168 enables a user of the defibrillator to take photos or video streams of data of the patient throughout the defibrillation process so that the condition of the patient may be recorded throughout defibrillation for use in connection with the defibrillation or for some post-defibrillation purpose, such as for use by medical professionals in providing post-defibrillation treatment or for use by coaches on the network in providing more effective coaching services going forward.

As another example, the ultrasound 1166 enables the user to take ultrasound measurements of a patient during the defibrillation process to provide imaging information of the internal structure of a patient during defibrillation or for use in post-defibrillation medical treatment or coaching applications. The display 1170 may allow a monitor, for instance, to be connected to the data processor module to allow for a broader or easier viewing of information that is either being displayed on the display of the defibrillator; is being generated by the data processor module and not displayed on the defibrillator display; is generated by a device external to the data module that is part of the network supporting the data processor module and is providing coaching to the user of the defibrillator; or other information. The display 1170 may provide a supplemental display to the display that may be available on the defibrillator and/or data processor module or display 970 may provide the only display available to the user of the data processor module and/or the defibrillator. The display 1170 may allow more people to view the defibrillation process. It may also allow people who are using the defibrillator and/or the data processor module to view a larger screen than may be available on the data processor module or defibrillator As illustrated in FIG. 11, the display 1170, video device 1168, ultrasound 1166, printer 1164, and partner devices 1162 are connected to the data processor module to provide bidirectional data communication over data communication link 1121 via utility connect 682, which is illustratively a USB connector port in this illustrative example. It will be appreciated that these functions could also be provided to the data processor module through any other wired connection or through a wireless connection according to this disclosure. The foregoing list of devices that may be connected with the data processor module are illustrative only. It will be appreciated that any other device may be tethered to the data processor module to provide the data processor module with additional functionality for use by the user of the defibrillator during a defibrillation procedure FIG. 11 further shows further functionality that the network may provide the data processor module in supporting the user of the defibrillator in this case through Wi-Fi module 684. It will be appreciated that these functions could also be provided to the data processor module through a wired connection. As illustrated in FIG. 11, the Wi-Fi module 684 enables wireless communication over data communication link 1123 between the data processor module and a computer 1108, a net server 71111, a tablet 1174, a team display 1174, and an access point 1176. The server 1110 has been previously described The tablet is an example of a mobile computing device in the form of a tablet that may wirelessly communicate with the data processor module via Wi-Fi module 1193 of the data processor module. Alternatively, any mobile computing device may be used in place of or in addition to the tablet, including a laptop computer, a smart phone, or any mobile computing device. These mobile computing devices may allow medical professionals and others to communicate with the data processor module and the data processor module and as a part of the network in providing assisted coaching to the user of the defibrillator through the data processor module of this disclosure. Team display 1194 may be a monitor or a flat screen TV; and is illustratively a large flat screen TV that allows groups of professionals to observe data provided by the data processor module or by another network device for the purpose of coaching the user of the defibrillator through the data module of this disclosure.

Figure 12:
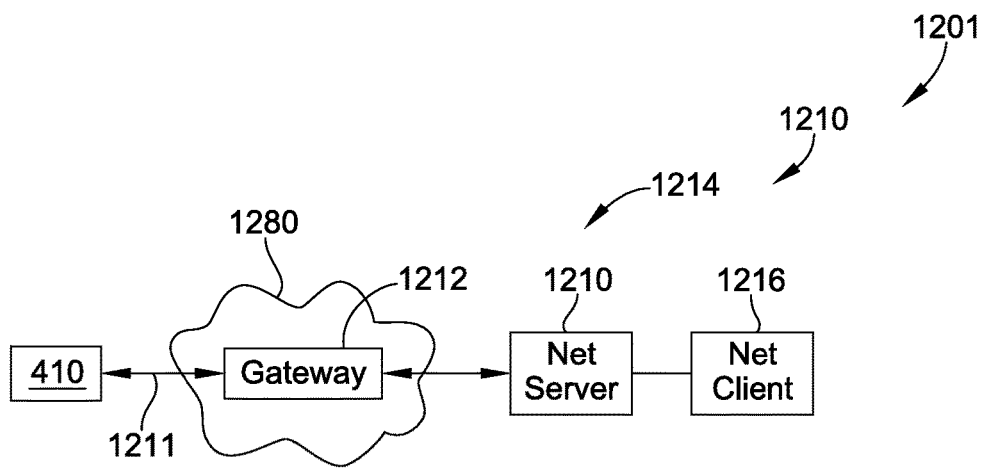
FIG. 12 illustrates the dual processor defibrillator of the defibrillator system of FIG. 4 engaging a network comprising a server and a client in connection with coaching a user of the defibrillator.

FIG. 12 illustrates a defibrillator system 1201 comprising the use defibrillator system 410 of FIGS. 4, 5. 6 and a network 1214 comprising a net server 1210 and a net client 1216 for coaching a user of the defibrillator. In this example, the net server 1210 and net client are in a private network 1214 and the defibrillator is outside that private network. FIG. 12 shows that the defibrillator may establish communication with server 1210 and client 1216 by going through cloud 1280 (in like description and operation as cloud 1180 in FIG. 11). In this example, the private network 1214 is provided with a gateway 1212 to the cloud 1280. The gateway provides a public portal to the private network that is physically addressable and hence reachable from the public network. In this example, the data processor module reaches the server 1210 by addressing the gateway 1212 to the private network 1214. The data processor module may reach the gateway through a Wi-Fi access port such as shown in FIG. 11. Alternatively, the data processor module may reach the gateway using WAN or using other communication technologies. The gateway may validate the defibrillator and then switch the data communication link 1211 that has been established between the gateway and the data processor module over to the server 1210 which is connected to the client 1216. This enables the client to communicate with the data processor module and the defibrillator in order to provide more robust coaching to the user of the defibrillator.

The network 1214 may support transmission of relevant patient data from the defibrillator 410 in the field to emergency departments, cardiac catherization labs, and other cardiac care locations to enable prompt and optimal diagnosis and treatment or appropriate post-review of the data by qualified medical personal. The network 1214 also enables organizations to manage their material assets and provides tools for remote physician consultation through the use of network consulting application.

Network 1214 may also provide event patient reports and data. Any report or data transaction that occurs during a patient monitoring or therapy event may be transmitted by the defibrillator to the net server 1210. The patient event data may assist qualified medical personnel in making accurate diagnosis, disposition, and therapy decisions. Event patient reports created by a defibrillator may be transferred through defibrillator to the net server 1210. The net server 1210 may be in a private network or a public network. If the net server 1210 is in a public network, the net PC gateway 1212 may be used for the data processor module to reach the network in which net server 1210 resides as previously described. Through the net PC gateway, the data processor module may establish bidirectional data communication with the net server for the purpose of transmitting patient event data from the defibrillator to the net server from which third party monitoring devices may retrieve the data and communicate with the defibrillator for the purpose of coaching the user of the defibrillator.

The net server may also enable reports to be generated from the data taken from the patient event and transmitted as needed after the event. This information may be useful in post-event analysis to support post-event medical treatment. For example, non-real-time data transfers of ePCR reports may be used in post-event analysis to document the treatment, patient state, and diagnosis provided by pre-hospital care providers. This information may also be useful as data for use in post-event training of medical professionals in order to train medical professionals to provide better coaching in connection with future events.

One application for use with the defibrillator is an event service that allows for the scheduled downloading of data from the defibrillator for storage in the data processor module or for pass-through to an external device through the data processor module acting as proxy for the external device. In either case, the data processor 480 may be configured to execute the instance of the event service provided by the server application in order to provide data communications from the defibrillator to the data processor module or to an external device through the data processor module acting as proxy. In one illustrative embodiment, the external device may be a server. Hence, the event service may be used to enable data communications to pass from the defibrillator to the data processor module for use by the data processor module or to the external device, through the data processor module acting as proxy, for use by the external device.

In the foregoing example, the server event service that enables scheduled downloading of data communications from the defibrillator resides on the data processor module as a client. Alternatively, the event service that provides data communications from the data processor module may be configured to reside on a computer. In either case, this event servicing application providing the instructions for the data processor of the data processor module to download defibrillator data advantageously enables the defibrillator system of this disclosure to provide scheduled downloads of defibrillator data to the data processor module or to the external device through the data processor module acting as a proxy.

Advantageously, the transmission of the data by the event service that enables data communications from the defibrillator to the data processor module to either use or pass through to an external device may occur at a predetermined period of time. The predetermined period of time at which the transmission of data by the event service that provides data communications from the data processor module from the defibrillator may illustratively occur substantially at or about 3 o'clock in the morning. Illustratively, the 3 o'clock in the morning time may be based on the time zone in which the defibrillator is being used. This allows the download of data from the defibrillator to occur at a time of the day when the defibrillator is least likely to be used. Where a defibrillator system of this disclosure is being managed across several time zones, the 3 o'clock in the morning time may be based on one of the time zones within that managed region.

While the preferred time of day for the download of data to occur is at or around 3 o'clock in the morning for the reasons previously discussed, it will be appreciated that the predetermined period of time at which the transmission of data by the event service that provides data communications from the data processor module from the defibrillator may be other than 3 o'clock in the morning and may also be managed in other ways. For instance, the predetermined period of time at which the transmission of data by the event service that provides data communications from the data processor module from the defibrillator may be scheduled to occur once a day. Alternatively, it may be scheduled to occur more than once a day. In addition, it may be scheduled to occur every other day, weekly, or at other regular or irregular periods of time. Where irregular periods of time are used, a random number generator may be used to instruct the event service what time to make the downloads each day. As another example, the predetermined period of time at which the transmission of data by the event service that provides data communications from the data processor module from the defibrillator may occur between the hours of midnight and 6 am in the morning. The defibrillator may come from the factory preprogrammed with a specific time for the download to occur. Alternatively, the specific time may be provided to the defibrillator at a later point in time in connection with an update to software or configuration settings. Illustratively, the specific time may be included in rules that may be downloaded to a defibrillator at any time. For instance, a rule may prescribe that the download is to occur at 3 o'clock in the morning unless the defibrillator is being used at that time. If the defibrillator is being used at 3 o'clock in the morning, the rule may prescribe that the download will occur at a predetermined period of time after the defibrillator has last been used. If this programmed predetermined period of time after defibrillator use is one hour and the last activity of the defibrillator is confirmed by the data processor module to be 3:27 am, then the foregoing rule would schedule the next download of data one hour later, or at 4:27 am in the morning, on the same day.

As previously indicated, the transmission of the data by the event service that provides data communications from the data processor module from the defibrillator may be to a server. Alternatively, it may be to a computer which is not configured to serve other computers. In the event the communication of the downloaded data from the defibrillator is to server, the download to the server may be within a private network or may occur over the public network such as over the internet. In the case of a download of data over a public network, the transmission may occur through gateway as shown and described in connection with FIG. 11.

While the foregoing event service has been described in connection with data transfers, it will be appreciated that the network may likewise schedule downloads of software, or downloads or uploads of other information all for the purpose of enhancing the defibrillation and coaching process.

Figure 13:
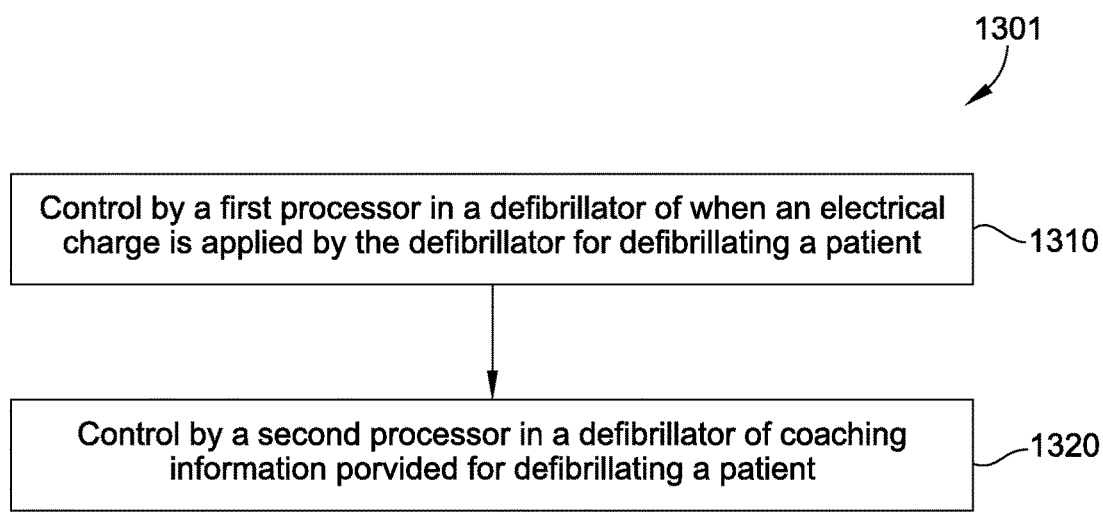
FIG. 13 is a flowchart for use of the dual processor defibrillator of the defibrillator system in applying a charge and coaching a user of the defibrillator.

FIG. 13 shows a method 1301 of the present disclosure for enhancing a defibrillation process involving a defibrillator including an energy storage device for storing an electrical charge and a defibrillator processor. The method includes the step of controlling 1310 by a first processor when an electrical charge is applied by the defibrillator for defibrillating a patient; and controlling 1320 by a second processor coaching information provided for defibrillating a patient. In an alternative embodiment the method includes the step of: sharing a resource between the first processor and the second processor. The shared resource may be a display.

In an alternative method, the method may further comprise the step of: configuring the first processor as a slave processor; configuring the second processor as a master processor; the second processor controlling the first processor in controlling the first processor when an electrical charge is applied by the defibrillator for defibrillating a patient. Additionally, the method may include the step of polling the first processor by the second processor to determine whether the second processor is properly controlling when an electrical charge is applied by the defibrillator for defibrillating a patient. Further, the method may include the step of transmitting data by the data processor from the defibrillator to one or more external devices for use by the one or more external devices in coaching the defibrillator.

In an alternative method, the method further includes the step of: receiving data by the data processor from one or more external devices for use in coaching the defibrillator. The step of transmitting data from the defibrillator to the one or more external devices may be for use by the one or more external devices in a post-defibrillation treatment. The step of transmitting the data transmitted from the defibrillator to the one or more external devices may be for use by the one or more external devices in asset management.

In an alternative method, the method may include the step of scheduling a polling of the defibrillator by the one or more external devices to determine the existence of data residing in the defibrillator. The polling may be scheduled to occur at a predetermined period of time. The method may further include the step of downloading software updates to the defibrillator by the one or more external devices. There is thus disclosed a defibrillator is provided with two processors for enhancing the defibrillation process. A first processor is dedicated to controlling when an electrical charge is applied to a patient. A second processor is dedicated to data operations for enhancing the coaching of the defibrillation process. The second data processor is in communication with one or more external devices for transmission and receipt of network data for further enhancing the coaching process. The second data processor allows both the defibrillator to be maintained with updated network data and software and the one or more external devices to be maintained with updated defibrillator data. Independent controllers provide multiple processing paths on critical charge and coaching functions; with the second data processor further providing redundancy control in the event of any malfunction of the first charge processor.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

We claim:

1. An external defibrillator comprising:
   a defibrillator processor module for storing and applying an electrical charge for defibrillating a patient, the defibrillator processor module including a defibrillator processor for controlling when the electrical charge is applied for defibrillating a patient;
   and a data processor module configured to control operations not essential for the survival of the patient, the data processor module including a data processor separate from the defibrillator processor,
   wherein the defibrillator processor is isolated in its processing from the processing done by the data processor, and wherein the data processor is configured to provide redundancy control in the event of a malfunction of the defibrillator processor.

2. The external defibrillator of claim 1 wherein the defibrillator processor module further comprises:
   an energy storage device for storing an electrical charge;
   a defibrillation port;
   a display; and
   a defibrillator data connect port
   wherein the defibrillator processor is configured to control the display and data communications over the defibrillator data connect port and when an electrical charge is applied to the defibrillation port for defibrillating a patient.

3. The external defibrillator of claim 1 wherein the data processor module further comprises:
   a memory unit configured for storing instructions executable by the data processor;
   a display unit configured to display coaching information;
   a communication module configured to transmit and receive coaching information from an external utility;
   a user interface configured for entering data;
   a bus interface configured to enable electrical communications between the data processor, the memory unit, the display unit, the communication module and the user interface; and
   wherein the data processor is configured to control the memory unit, the display unit, the communication module, and the user interface for controlling the coaching information provided.

4. The external defibrillator of claim 3 wherein the communication module further comprises a wireless communication module, the data processor being configured to control the wireless communication module for controlling the coaching information provided.

5. The external defibrillator of claim 4 wherein the wireless communication module is based on a protocol take from the group of protocols consisting of Wi-Fi, Ultra Wideband, NFC, Bluetooth, and ZigBee.

6. The external defibrillator of claim 3 wherein the communication module further comprises a network data connect module including a data connect port, the data processor being configured to control the network data connect module for controlling the coaching information provided.

7. The external defibrillator of claim 6 wherein the network data connect is based on a protocol taken from the group of protocols consisting of SPI, Ethernet, and USB.

8. The external defibrillator of claim 3 wherein the data processor module further comprises a parameter module configured for providing patient parameter data, the data processor being configured to control the parameter module for controlling the coaching information provided.

9. The external defibrillator of claim 3 wherein the data processor module resides in a package that is physically attached to the outside of the defibrillator.

10. The external defibrillator of claim 3 wherein the data processor module resides in a device that is separate from the defibrillator, the data processor being in communication with the defibrillator through a communication module included in the separate device.

11. The external defibrillator of claim 10 wherein the separate device provides audio, video, or audio-visual coaching and/or serves as a data collection tool in support of the treatment of a patient with the defibrillator.

12. The external defibrillator of claim 3 wherein the data processor module resides inside the defibrillator.

13. The external defibrillator of claim 8:
   wherein patient parameter data from the parameter module is displayed on the data processor display.

14. The external defibrillator of claim 1 further comprising:
   a shared resource configured for sharing between the defibrillator processor module and the data processor module; and
   a bus configured for enabling electrical communications between each of the defibrillator processor module and the data processor module and the shared resource.

15. The external defibrillator of claim 14 wherein the shared resource is a display.

16. The external defibrillator of claim 1 further comprising:
   an interprocessor control line configured for enabling control by the defibrillator processor over the data processor.

17. The external defibrillator of claim 16 wherein the control is for power management of the data processor.

18. The external defibrillator of claim 16 wherein the control is for power management of the external devices connected to the data processor.

19. The external defibrillator of claim 1 further comprising:
an interprocessor communication unit configured for transferring data between the defibrillator processor and the data processor; and
hardwire control lines for controlling the transfer of the data.

20. The external defibrillator of claim 19 wherein the inter processor interface bus comprises a message based communication link.

21. The external defibrillator of claim 19 wherein a semaphore module is configured for enabling coordinated access to the shared resource by the defibrillator processor module and the data processor module.

22. The external defibrillator of claim 19 wherein the interprocessor interface bus comprises a tightly coupled memory unit.

23. The external defibrillator of claim 1 further comprising:
a global memory unit;
and control lines for enabling either of the defibrillator processor and the data processor to assert control over the global memory unit for transferring data to the global memory unit for transfer to the other processor.

24. The external defibrillator of claim 1 wherein the data processor periodically polls the defibrillator processor to determine the functioning of the defibrillator processor and activates fail safe measures based on a predetermined response.

25. The external defibrillator of claim 1:
wherein the data processor being further configured to execute an instance for providing data communications between the data processor and an external utility.

26. The external defibrillator of claim 25 wherein the instance is an event service.

27. The external defibrillator of claim 25 wherein the external utility is a computer.

28. The external defibrillator of claim 27 wherein the computer is a server.

29. The external defibrillator of claim 28 wherein the transmission of the data by the instance that provides data communications between the defibrillator and the server is via a network.

30. The external defibrillator of claim 29 wherein the network over which the data communications between the defibrillator and the server is the internet.

31. The external defibrillator of claim 25 wherein the one or more external devices is a computer taken from the group consisting of a server, a personal computer, a tablet, a mobile computing device, a video device, an ultrasound device, and a printer.

32. The external defibrillator of claim 1, wherein the data processor module is configured to store and to provide coaching information for use for defibrillating a patient.

33. The external defibrillator of claim 1, wherein the data processor is able to control the defibrillator processor in a master slave relationship.

34. An external defibrillator comprising:
a defibrillator processor module for storing and applying an electrical charge for defibrillating a patient, the defibrillator processor module including a defibrillator processor for controlling when the electrical charge is applied for defibrillating a patient; and
a data processor module, including a data processor separate from the defibrillator processor configured to control operations not essential for the survival of the patient, the data processor module executing an event service that provides for scheduled downloading of data from the defibrillator to an external computing device using the data processor module as a proxy,
wherein the defibrillator processor is isolated in its processing from the processing done by the data processor.

35. The external defibrillator of claim 34 wherein communication and control of the data processor module is configured to avoid interfering with the defibrillator processor module control of the electrical charge applied.

36. The external defibrillator of claim 34 wherein the non-survival essential operations is coaching from the group of coaching types consisting of extended monitoring, extended diagnosis, and interventional treatments.

37. The external defibrillator of claim 34 wherein the application of the electrical charge by the defibrillator processor module is isolated from the control operations of the data processor module.

38. The external defibrillator of claim 34, wherein the data processor is configured to selectively control the defibrillator processor.

39. The external defibrillator of claim 34, wherein the event service provides for scheduled downloading of data from the defibrillator at a predetermined period of time.

* * * * *